United States Patent [19]
Grabstein et al.

[11] Patent Number: 5,985,262
[45] Date of Patent: Nov. 16, 1999

[54] METHOD OF TREATMENT WITH EPITHELIUM DERIVED T-CELL FACTOR

[75] Inventors: Kenneth H. Grabstein, Mercer Island; Dirk M. Anderson; June R. Eisenman, both of Seattle; Victor Fung, Redmond; Charles Rauch, Bainbridge Island, all of Wash.

[73] Assignee: Immunex Corporation, Seattle, Wash.

[21] Appl. No.: 08/794,524

[22] Filed: Feb. 3, 1997

Related U.S. Application Data

[62] Division of application No. 08/726,817, Oct. 4, 1996, Pat. No. 5,707,616, which is a division of application No. 08/393,305, Feb. 22, 1995, Pat. No. 5,574,138, which is a continuation-in-part of application No. 08/233,606, Apr. 22, 1994, abandoned, which is a continuation-in-part of application No. 08/031,399, Mar. 8, 1993, Pat. No. 5,552,303.

[51] Int. Cl.$^6$ .......................... A61K 38/20; C07K 14/54; C12N 15/24
[52] U.S. Cl. .................. 424/85.2; 424/184.1; 424/198.1; 514/2; 514/8; 514/12; 514/885; 530/351; 536/23.1; 536/23.51; 536/24.3
[58] Field of Search ..................... 514/2, 8, 12; 424/85.1, 424/85.2, 184.1, 198.1; 530/351; 536/23.1, 23.5, 24.3

[56] References Cited

U.S. PATENT DOCUMENTS 5,707,616   1/1998   Grabstein et al. ..................... 424/85.2

OTHER PUBLICATIONS

Grabstein et al., "Cloning of a T Cell Growth Factor That Interacts with the βChain of the Interleukin–2 Receptor," *Science* 264: 965–968, 1994.

McMahan et al., "A novel IL–1 receptor, cloned from B cells by mammalian expression, is expressed in many cell types," *EMBO Journal* 10(10):2821–2832, 1991.

Arai et al. (1990) Ann. Rev. Biochem. vol. 59, pp. 783–836.

Fahey et al. (1992) Clin. exp. Immunol. vol. 88, pp. 1–5.

Johnston et al. (1993) Science vol. 260, pp. 1286–1293.

Bowie et al. (1990) Science vol. 247, pp. 1306–1310.

Levy (1993) Microbiological Reviews, vol. 57, No. 1, pp. 183–289.

Callard & Gearing (1994) The Cytokine Facts Book. Academic Press, San Diego, CA, pp. 39–40.

*Primary Examiner*—Prema Mertz
*Attorney, Agent, or Firm*—Seed and Berry LLP

[57] ABSTRACT

Nucleic acid sequences which encode biologically active EMF, expression vectors which direct the expression of ETF, ETE polypeptides, antibodies which specffically bind ETF and processes for preparing the same are disclosed. Also disclosed are methods for treating or preventing gastrointestinal diseases and HIV or HIV-associated diseases.

3 Claims, 10 Drawing Sheets

AAC TGG GTG AAT GTA ATA AGT GAT TTG AAA AAA ATT GAA GAT CTT ATT
Asn Trp Val Asn Val Ile Ser Asp Leu Lys Lys Ile Glu Asp Leu Ile

CAA TCT ATG CAT ATT GAT GCT ACT TTA TAT ACA GAA AGT GAT GTT CAC
Gln Ser Met His Ile Asp Ala Thr Leu Tyr Thr Glu Ser Asp Val His

CCC AGT TGC AAG GTA ACA GCA ATG AAG TGC TTT CTC TTG GAG TTG CAA
Pro Ser Cys Lys Val Thr Ala Met Lys Cys Phe Leu Leu Glu Leu Gln

GTT ATT TCA CAT GAG TCC GGA GAT ATT CAT GAT ACA GTA GAA
Val Ile Ser His Glu Ser Gly Asp Ile His Asp Thr Val Glu

AAT CTT ATC ATC CTA GCA AAC AAC ATC TTG TCT AAT GGG AAT ATA
Asn Leu Ile Ile Leu Ala Asn Asn Ile Leu Ser Asn Gly Asn Ile

ACA GAA TCT GGA TGC AAA GAA TGT GAG GAA CTA GAG GAA AAA AAT ATT
Thr Glu Ser Gly Cys Lys Glu Cys Glu Glu Leu Glu Glu Lys Asn Ile

AAA GAA TTT TTG CAG AGT TTT GTA CAT ATT GTC CAA ATG TTC ATC AAC
Lys Glu Phe Leu Gln Ser Phe Val His Ile Val Gln Met Phe Ile Asn

ACT TCT TGA
Thr Ser

*Fig. 1*

```
AAC TGG GTG AAT GTA ATA AGT GAT TTG AAA ATT GAA GAT CTT ATT
Asn Trp Val Asn Val Ile Ser Asp Leu Lys Ile Glu Asp Leu Ile

CAA TCT ATG CAT ATT GAT GCT ACT TTA TAT ACG GAA AGT GAT GTT CAC
Gln Ser Met His Ile Asp Ala Thr Leu Tyr Thr Glu Ser Asp Val His

CCC AGT TGC AAA GTA ACA GCA ATG AAG TGC TTT CTC TTG GAG TTA CAA
Pro Ser Cys Lys Val Thr Ala Met Lys Cys Phe Leu Leu Glu Leu Gln

GTT ATT TCA CTT GAG TCC GGA GAT GCA AGT ATT CAT GAT ACA GTA GAA
Val Ile Ser Leu Glu Ser Gly Asp Ala Ser Ile His Asp Thr Val Glu

AAT CTG ATC CTA GCA AAC AGT TGT TCT GAG AAT GGG AAA AAT ATT GTA
Asn Leu Ile Leu Ala Asn Ser Cys Ser Glu Asn Gly Lys Asn Ile Val

ACA GAA TCT GGA TGC AAA GAA TGT GAG GAA CTG GAG GAA AAA ATT
Thr Glu Ser Gly Cys Lys Glu Cys Glu Glu Leu Glu Glu Lys Ile

AAA GAA TTT TTG CAG AGT TTT GTA CAT ATT GTC CAA ATG TTC ATC AAC
Lys Glu Phe Leu Gln Ser Phe Val His Ile Val Gln Met Phe Ile Asn

ACT TCT TGA
Thr Ser
```

*Fig. 2*

CV-1/EBNA
DMEM serum free
bioreactors

YM30 Spiral cartridge conc.

add ammonium sulfate
HEPES pH 8.5

Phenyl Sepharose CL-4B
0.2M ammonium sulfate
20 mM HEPES pH 8.5
elute with 10mM HEPES pH 8.5 add NaCl to 1.6 mS/cm

DEAE Sephacel
10mM HEPES pH 8.5
0.14 to 0.3 M NaCl gradient dilute to 1.2 mS/cm

Mono Q
10mM HEPES pH 8.5
0.1 to 0.5 M NaCl gradient

HPLC C4 reverse phase (Vydac, 46 X 25 cm, 5u)
0.1% TFA to 0.1% TFA/100% AcN, 1ml/min 0 to 45% AcN  1%/min
45-60% AcN  0.5%/min
60-100% AcN  2%/min

HPLC C4 reverse phase (Vydac, 46X25cm, 5u)
0.1% TFA to 0.1% TFA/60% n-propanol
0.5ml/min
0.5%/min gradient

SDS PAGE 14%, reducing

PVDF

N-terminal protein sequence

*Fig. 3*

```
ATGAGAATTTCGAAACCACATTTGAGAAGTATTTCCATCCAGTGCTACTT
||||||||||||||||||||||||||||||||||||||||||||||||| |
ATGAGAATTTCGAAACCACATTTGAGAAGTATTTCCATCCAGTGCTACCT

GTGTTACTTCTAAACAGTCATTTCTAACTGAAGCTGGCATTCATGTCT
|||||||||||||| |||||||||||||||||||||||||||||||||
GTGTTACTTCTAAAGAGTCATTTCTAACTGAAGCTGGCATTCATGTCT

TCATTTGGCTGTTTCAGTGCAGGGCTTCCTAAAACAGAAGCCAACTGG
||||||||||||||||||||||||||| ||||||||||||||||||||
TCATTTGGCTGTTTCAGTGCAGGGCTCCCTAAAACAGAAGCCAACTGG

GTGAATGTAATAAGTGATTTGAAAAAATTGAAGATCTTATTCAATCTAT
|||||||||||||||||||||||||||||||||||||||||||||||||
GTGAATGTAATAAGTGATTTGAAAAAATTGAAGATCTTATTCAATCTAT

GCATATTGATGCTACTTTATATACGGAAAGTGATGTTCACCCCAGTTGCA
||||||||||||||||||||||||| |||||||||||||||||||||||
GCATATTGATGCTACTTTATATACAGAAAGTGATGTTCACCCCAGTTGCA

AAGTAACAGCAATGAAGTGCTTTCTCTTGGAGTTACAAGTTATTTCACTT
| |||||||||||||||||||||||||||||||| ||||||||||||| |
AGGTAACAGCAATGAAGTGCTTTCTCTTGGAGTTGCAAGTTATTTCACAT

GAGTCCGGAGATGCAAGTATTCATGATACAGTAGAAAATCTGATCATCCT
|||||||||||| || |||||||||||||||||||||||||| |||||||
GAGTCCGGAGATACAGATATTCATGATACAGTAGAAAATCTTATCATCCT

AGCAAACAACAGTTTGTCTTCTAATGGGAATGTAACAGAATCTGGATGCA
|||||||||| |||||||||||||||||||| ||||||||||||||||||
AGCAAACAACATCTTGTCTTCTAATGGGAATATAACAGAATCTGGATGCA

AAGAATGTGAGGAACTGGAGGAAAAAATATTAAAGAATTTTTGCAGAGT
||||||||||||||||| |||||||||||||||||||||||||||||||
AAGAATGTGAGGAACTAGAGGAAAAAATATTAAAGAATTTTTGCAGAGT

TTTGTACATATTGTCCAAATGTTCATCAACACTTCTTGA
|||||||||||||||||||||||||||||||||||||||
TTTGTACATATTGTCCAAATGTTCATCAACACTTCTTGA
```

*Fig. 4*

```
  1  MRISKPHLRSISIQCYLCLLLNSHFLTEAGIHVFILGCFSAGLPKTEANW   50
     |||||||||||||||||||||||| :|||||||||||||||||||||||||
  1  MRISKPHLRSISIQCYLCLLLKSHFLTEAGIHVFILGCFSAGLPKTEANW   50

51  VNVISDLKKIEDLIQSMHIDATLYTESDVHPSCKVTAMKCFLLELQVISL  100
     |||||||||||||||||||||||||||||||||||||||||||||||||:
 51  VNVISDLKKIEDLIQSMHIDATLYTESDVHPSCKVTAMKCFLLELQVISH  100

101  ESGDASIHDTVENLIILANNSLSSNGNVTESGCKECEELEEKNIKEFLQS  150
     ||||:|||||||||||||||:|||||||:|||||||||||||||||||||
101  ESGDTDIHDTVENLIILANNILSSNGNITESGCKECEELEEKNIKEFLQS  150

151  FVHIVQMFINTS*  163
     |||||||||||||
151  FVHIVQMFINTS*  163
```

Fig. 5

SEQUENCE LISTING (1) GENERAL INFORMATION:

(iii) NUMBER OF SEQUENCES: 15

(2) INFORMATION FOR SEQ ID NO:1:

```
       (i) SEQUENCE CHARACTERISTICS:
           (A) LENGTH: 489 base pairs
           (B) TYPE: nucleic acid
           (C) STRANDEDNESS: single
           (D) TOPOLOGY: linear (ix) FEATURE:
           (A) NAME/KEY: CDS
           (B) LOCATION: 1..489

(xi) SEQUENCE DESCRIPTION: SEQ ID NO:1:

ATG AGA ATT TCG AAA CCA CAT TTG AGA AGT ATT TCC ATC CAG TGC TAC        48
Met Arg Ile Ser Lys Pro His Leu Arg Ser Ile Ser Ile Gln Cys Tyr
 1               5                  10                  15

TTG TGT TTA CTT CTA AAC AGT CAT TTT CTA ACT GAA GCT GGC ATT CAT        96
Leu Cys Leu Leu Leu Asn Ser His Phe Leu Thr Glu Ala Gly Ile His
             20                  25                  30

GTC TTC ATT TTG GGC TGT TTC AGT GCA GGG CTT CCT AAA ACA GAA GCC       144
Val Phe Ile Leu Gly Cys Phe Ser Ala Gly Leu Pro Lys Thr Glu Ala
         35                  40                  45

AAC TGG GTG AAT GTA ATA AGT GAT TTG AAA AAA ATT GAA GAT CTT ATT       192
Asn Trp Val Asn Val Ile Ser Asp Leu Lys Lys Ile Glu Asp Leu Ile
 50                  55                  60

CAA TCT ATG CAT ATT GAT GCT ACT TTA TAT ACG GAA AGT GAT GTT CAC       240
Gln Ser Met His Ile Asp Ala Thr Leu Tyr Thr Glu Ser Asp Val His
 65                  70                  75                  80

CCC AGT TGC AAA GTA ACA GCA ATG AAG TGC TTT CTC TTG GAG TTA CAA       288
Pro Ser Cys Asn Val Thr Ala Met Lys Cys Phe Leu Leu Glu Leu Gln
                 85                  90                  95

GTT ATT TCA CTT GAG TCC GGA GAT GCA AGT ATT CAT GAT ACA GTA GAA       336
Val Ile Ser Leu Glu Ser Gly Asp Ala Ser Ile His Asp Thr Val Glu
             100                 105                 110

AAT CTG ATC ATC CTA GCA AAC AAC AGT TTG TCT TCT AAT GGG AAT GTA       384
Asn Leu Ile Ile Leu Ala Asn Asn Ser Leu Ser Ser Asn Gly Asn Val
         115                 120                 125

ACA GAA TCT GGA TGC AAA GAA TGT GAG GAA CTG GAG GAA AAA AAT ATT       432
Thr Glu Ser Gly Cys Lys Glu Cys Glu Glu Leu Glu Glu Lys Asn Ile
     130                 135                 140

AAA GAA TTT TTG CAG AGT TTT GTA CAT ATT GTC CAA ATG TTC ATC AAC       480
Lys Glu Phe Leu Gln Ser Phe Val His Ile Val Gln Met Phe Ile Asn
145                 150                 155                 160

ACT TCT TGA                                                            489
Thr Ser (2) INFORMATION FOR SEQ ID NO:2:

(i) SEQUENCE CHARACTERISTICS:
           (A) LENGTH: 162 amino acids
           (B) TYPE: amino acid
           (D) TOPOLOGY: linear (ii) MOLECULE TYPE: protein (xi) SEQUENCE DESCRIPTION: SEQ ID NO:2:

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
```

```
                 65                  70                  75                  80
Pro Ser Cys Lys Val Thr Ala Met Lys Cys Phe Leu Leu Glu Leu Gln
                         85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser (2) INFORMATION FOR SEQ ID NO:3:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:3:

Asn Trp Val Asn Val Ile Ser Asp Leu Lys Lys Ile Glu Asp Leu Ile
1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser (2) INFORMATION FOR SEQ ID NO:4:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..489

(xi) SEQUENCE DESCRIPTION: SEQ ID NO:4:

ATG AGA ATT TCG AAA CCA CAT TTG AGA AGT ATT TCC ATC CAG TGC TAC      48
Met Arg Ile Ser Lys Pro His Leu Arg Ser Ile Ser Ile Gln Cys Tyr
1               5                  10                  15

CTG TGT TTA CTT CTA AAG AGT CAT TTT CTA ACT GAA GCT GGC ATT CAT      96
Leu Cys Leu Leu Leu Lys Ser His Phe Leu Thr Glu Ala Gly Ile His
            20                  25                  30

GTC TTC ATT TTG GGC TGT TTC AGT GCA GGG CTC CCT AAA ACA GAA GCC     144
Val Phe Ile Leu Gly Cys Phe Ser Ala Gly Leu Pro Lys Thr Glu Ala
        35                  40                  45
```

```
AAC TGG GTG AAT GTA ATA AGT GAT TTG AAA AAA ATT GAA GAT CTT ATT      192
Asn Trp Val Asn Val Ile Ser Asp Leu Lys Lys Ile Glu Asp Leu Ile
     50                  55                  60

CAA TCT ATG CAT ATT GAT GCT ACT TTA TAT ACA GAA AGT GAT GTT CAC      240
Gln Ser Met His Ile Asp Ala Thr Leu Tyr Thr Glu Ser Asp Val His
 65                  70                  75                  80

CCC AGT TGC AAG GTA ACA GCA ATG AAG TGC TTT CTC TTG GAG TTG CAA      288
Pro Ser Cys Lys Val Thr Ala Met Lys Cys Phe Leu Leu Glu Leu Gln
                 85                  90                  95

GTT ATT TCA CAT GAG TCC GGA GAT ACA GAT ATT CAT GAT ACA GTA GAA      336
Val Ile Ser His Glu Ser Gly Asp Thr Asp Ile His Asp Thr Val Glu
                100                 105                 110

AAT CTT ATC ATC CTA GCA AAC AAC ATC TTG TCT TCT AAT GGG AAT ATA      384
Asn Leu Ile Ile Leu Ala Asn Asn Ile Leu Ser Ser Asn Gly Asn Ile
            115                 120                 125

ACA GAA TCT GGA TGC AAA GAA TGT GAG GAA CTA GAG GAA AAA AAT ATT      432
Thr Glu Ser Gly Cys Lys Glu Cys Glu Glu Leu Glu Glu Lys Asn Ile
        130                 135                 140

AAA GAA TTT TTG CAG AGT TTT GTA CAT ATT GTC CAA ATG TTC ATC AAC      480
Lys Glu Phe Leu Gln Ser Phe Val His Ile Val Gln Met Phe Ile Asn
145                 150                 155                 160

ACT TCT TGA                                                          489
Thr Ser
```

(2) INFORMATION FOR SEQ ID NO:5:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:5:

```
Met Arg Ile Ser Lys Pro His Leu Arg Ser Ile Ser Ile Gln Cys Tyr
 1               5                  10                  15

Leu Cys Leu Leu Leu Lys Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser His Glu Ser Gly Asp Thr Asp Ile His Asp Thr Val Glu
                100                 105                 110

Asn Leu Ile Ile Leu Ala Asn Asn Ile Leu Ser Ser Asn Gly Asn Ile
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

(2) INFORMATION FOR SEQ ID NO:6:

(i) SEQUENCE CHARACTERISTICS:

(A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:6:

Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser His Glu Ser Gly Asp Thr Asp Ile His Asp Thr Val Glu
     50                  55                  60

Asn Leu Ile Ile Leu Ala Asn Asn Ile Leu Ser Ser Asn Gly Asn Ile
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
             100                 105                 110

Thr Ser (2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

TCGACTGGAA CGAGACGACC TGCT                                            24

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

GACCTTGCTC TGCTGGACGA                                                 20

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

AAYTGGGTNA AYGTNATH                                                   18

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

ACRTCNGAYT CNGTRTA                                                           17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:11:

ACRTCRCTYT CNGTRTA                                                           17

(2) INFORMATION FOR SEQ ID NO:12:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..345

(xi) SEQUENCE DESCRIPTION: SEQ ID NO:12:

```
AAC TGG GTG AAT GTA ATA AGT GAT TTG AAA AAA ATT GAA GAT CTT ATT        48
Asn Trp Val Asn Val Ile Ser Asp Leu Lys Lys Ile Glu Asp Leu Ile
 1               5                  10                  15

CAA TCT ATG CAT ATT GAT GCT ACT TTA TAT ACG GAA AGT GAT GTT CAC        96
Gln Ser Met His Ile Asp Ala Thr Leu Tyr Thr Glu Ser Asp Val His
            20                  25                  30

CCC AGT TGC AAA GTA ACA GCA ATG AAG TGC TTT CTC TTG GAG TTA CAA       144
Pro Ser Cys Lys Val Thr Ala Met Lys Cys Phe Leu Leu Glu Leu Gln
    35                  40                  45

GTT ATT TCA CTT GAG TCC GGA GAT GCA AGT ATT CAT GAT ACA GTA GAA       192
Val Ile Ser Leu Glu Ser Gly Asp Ala Ser Ile His Asp Thr Val Glu
50                  55                  60

AAT CTG ATC ATC CTA GCA AAC AAC AGT TTG TCT TCT AAT GGG AAT GTA       240
Asn Leu Ile Ile Leu Ala Asn Asn Ser Leu Ser Ser Asn Gly Asn Val
65                  70                  75                  80

ACA GAA TCT GGA TGC AAA GAA TGT GAG GAA CTG GAG GAA AAA AAT ATT       288
Thr Glu Ser Gly Cys Lys Glu Cys Glu Glu Leu Glu Glu Lys Asn Ile
                85                  90                  95

AAA GAA TTT TTG CAG AGT TTT GTA CAT ATT GTC CAA ATG TTC ATC AAC       336
Lys Glu Phe Leu Gln Ser Phe Val His Ile Val Gln Met Phe Ile Asn
            100                 105                 110

ACT TCT TGA                                                           345
Thr Ser *
        115
```

(2) INFORMATION FOR SEQ ID NO:13:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..345

(xi) SEQUENCE DESCRIPTION: SEQ ID NO:13:

```
AAC TGG GTG AAT GTA ATA AGT GAT TTG AAA AAA ATT GAA GAT CTT ATT        48
Asn Trp Val Asn Val Ile Ser Asp Leu Lys Lys Ile Glu Asp Leu Ile
```

```
                1               5                      10                    15
CAA TCT ATG CAT ATT GAT GCT ACT TTA TAT ACA GAA AGT GAT GTT CAC              96
Gln Ser Met His Ile Asp Ala Thr Leu Tyr Thr Glu Ser Asp Val His
                        20                  25                  30

CCC AGT TGC AAG GTA ACA GCA ATG AAG TGC TTT CTC TTG GAG TTG CAA             144
Pro Ser Cys Lys Val Thr Ala Met Lys Cys Phe Leu Leu Glu Leu Gln
            35                  40                  45

GTT ATT TCA CAT GAG TCC GGA GAT ACA GAT ATT CAT GAT ACA GTA GAA             192
Val Ile Ser His Glu Ser Gly Asp Thr Asp Ile His Asp Thr Val Glu
        50                  55                  60

AAT CTT ATC ATC CTA GCA AAC AAC ATC TTG TCT TCT AAT GGG AAT ATA             240
Asn Leu Ile Ile Leu Ala Asn Asn Ile Leu Ser Ser Asn Gly Asn Ile
65                      70                  75                  80

ACA GAA TCT GGA TGC AAA GAA TGT GAG GAA CTA GAG GAA AAA AAT ATT             288
Thr Glu Ser Gly Cys Lys Glu Cys Glu Glu Leu Glu Glu Lys Asn Ile
                    85                  90                  95

AAA GAA TTT TTG CAG AGT TTT GTA CAT ATT GTC CAA ATG TTC ATC AAC             336
Lys Glu Phe Leu Gln Ser Phe Val His Ile Val Gln Met Phe Ile Asn
                100                 105                 110

ACT TCT TGA                                                                 345
Thr Ser  *
        115

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:14:

Asn Trp Val Asn Val Ile
1               5

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:15:

Tyr Thr Glu Ser Asp Val
1               5
```

METHOD OF TREATMENT WITH EPITHELIUM DERIVED T-CELL FACTOR

CROSS-REFERENCE TO RELATED APPLICATIONS

This application is a division of pending U.S. patent application Ser. No. 08/726,817, filed Oct. 4, 1996 now U.S. Pat. No. 5,707,616; which application is a division of U.S. patent application Ser. No. 08/393,305, filed Feb. 22, 1995, issued as U.S. Pat. No. 5,574,138; which application is a continuation-in-part of U.S. patent application Ser. No. 08/233,606, filed Apr. 22, 1994, now abandoned; which application is a continuation-in-part of U.S. patent application Ser. No. 08/031,399, filed Mar. 8, 1993; issued as U.S. Pat. No. 5,552,303.

FIELD OF THE INVENTION

The present invention relates generally to a mammalian epithelium-derived T-ceil factor ("ETF") polypeptide. It more particularly relates to isolated mammalian ETF polypeptide sequences and derivatives thereof compositions containing mammalian ETF that induce T cell proliferation and differentiation, compositions containing mammalian ETF that induce B cell proliferation and secretion, compositions containing mammalian ETF that augment destruction of tumor cells or viral-infected cells, compositions containing mamrmalian ETF that augment anti-infectious disease immunity, and compositions containing mammalian ETF for preventing radio- and chemotherapy-induced toxicity.

BACKGROUND OF THE INVENTION

T-cells, also known as T-lymphocytes, are a class of immune effector cells. In peripheral tissues, T -cells can be divided into two broad groups based on their mutually exclusive expression of CD4 and CDS cell surface molecules. Typical $CD8^+$ T-cells become cytotoxic T-cells after activation and destroy antigen bearing target cells through direct cell contact. Activated $CD4^+$ T-cells generally provide positive signals, for example, "helper" function for B cells (that engages to antibody-forming cells) and, therefore, are called helper T-cells.

Six T-cell growth factors have previously been identified: Interleukin (IL)-2, -4, -7, -9, -12 and cofactor IL-10. Each of these will be discussed in turn below. Briefly, IL-2's open reading frame codes for a 15 kDa, 153-amno acid polypeptide. IL-2 is produced by certain T-cells and by large granular lymphocytes. IL-2 was originally discovered as a factor that would support long-term growth of human T-cells. In addition to T-cell growth, its effects include activation of natural killer (NK cells and lympholdne-activated killer (LAK) cells as well as cytotoxic T-cells ("CTL"), macrophages and promotion of B-cell growth.

IL-4 is a 15–20 kDa protein produced by activated T-cels, bone marrow stromal cells, and mast cells. The UL4 open reading frame codes for 140-amino acid murine IL-4 and 153-amino acid human IL-4. Originally, IL-4 was defined as a factor that activated B-cell growth and differentiation. Its effects also include macrophage activation and induction of class II MHC molecules, growth of some T-cell and mast cell lines, proliferation and CTL generation from human peripheral blood T-cells and enhancement of immunoglobulin production by B-cells. IL-4 also acts as a cofactor in growth of hematopoietic cells from stem cells, and plays an important role in the down-regulation of IL-2 induced NK cell and LAK cell activities. Human IL-4 is not active on murine cells.

IL-7 is a 20–25 kDa, 177 amino acid polypeptide produced by bone marrow and thymic stromal cells. Although it was originally described as a pre-B-cell growth factor, IL-7 supports the growth of pro-B-cells as well as pre-B-cells. IL-7 also induces proliferation and CTL generation from human peripheral blood T-cells, IL-2 receptor expression, IL-2 production, and proliferation in $CD4^+$ and $CD8^+$ cells. IL-7 also synergizes with IL-2 and increases thymic T-cell proliferation and induces proliferation of $CD4^-$ and $CD8^-$ thymocytes.

IL-9 is a 30–40 kDa, 144 amino acid polypeptide produced by activated T-lymphocytes. IL-9 was first identified as a helper T-cell growth factor. IL-9 stimulates erythroid development and enhances IL-3 induced proliferation of bone marrow-derived mast cells. It also modulates IgE and IgG production by B-cells in the presence of IL-4. Murine IL-9 is active on human cells, whereas human IL-9 does not act on murine cells.

Human IL-10 is a 16–20 kDa, 178-amino acid potypeptide produced by macrophages and TH2 but not TH1 T-helper cells. Like IL-2, IL-4 and IL-7, IL-10 has several different biological activities. IL-10 was discovered on the basis of its ability to inhibit cytokine production by activated T-cells. Both human and murine IL-10 are growth-stimulatory cofactors for thymocytes and T-cells in combination with IL-7 or IL-2 plus IL-4. IL-10 stimulates mast cell viability and growth in combination with IL-4 or IL-3 plus L-4. IL-10 also induces the IgG secretion and expression of MHC class II molecules on B-cells and increases their viability in culture.

IL-12 is constitutive or induced by phorbol ester and calcium ionophore in lymphoblastoid cell lines and is produced by LPS stimulated macrophages. IL-12 has a molecular weight of 70 kDa and an unusual heterodimeric structure, being formed of two disulfide-bonded glycoproteins. The larger of the two glycoprotein subunits is a 40 kDa, 328-amino acid polypeptide. The smaller glycoprotein subunit is a 35 kDa, 253-amino acid polypeptide. Both glycoprotein subunits are necessary for bioactivity. IL-12 induces the proliferation of activated T-cells of both the $CD4^+$ and $CD8^+$ subsets independently of IL-2. IL-12 also activates NK-cell-mediated cytotoxicity and synergizes with IL-2 to generate LAK cells. Unlike IL-2 and IL-7, but similar to IL-4, IL-12 causes little or no proliferation of resting peripheral blood mononuclear cells.

The present invention provides a new, previously unidentified T-cell growth factor, designated "Epithelium-derived T-cell Factor" ("ETF"), and further provides other related advantages.

SUMMARY OF THE INVENTION

As noted above, the present invention provides novel T-cell growth factors, hereinafter referred to as "Epithellum-derived T-cell Factors" ("ETF"). Briefly, within one aspect of the present invention isolated nucleic acid sequences are provided which encode biologically active ETF. Within one embodiment, such nucleic acid sequences may be selected from the group consisting of: (a) cDNA (both coding and non-coding strands) which encodes a mammalian ETF gene; (b) nucleic acid sequences which hybridize to the cDNA of (a) under moderate stringency conditions and which encode a biologically active ETF; and (c) nucleic acid sequence that are degenerate as a result of the genetic code to the nucleic acid sequences of (a) or (b), and which encode biologically active ETF. Within further embodiments, isolated nucleic acid sequences are provided comprising nucleotides 145 through 486 of either SEQ ID NOS 1 or 4. Also provided are expression vectors capable of directing the expression of any of the above-described nucleic acid sequences, host cells transformed or transfected with such expression vectors, as well as processes for preparing ETF, comprising the steps of culturing one or the above-described host cells under conditions which promote expression of ETF, and recovering ETF from the culture.

Within another aspect of the present invention, isolated biologically active ETF polypeptides are provided, wherein the ETF polypeptide is selected from the group consisting of: (a) a polypeptide having the amino acid sequence of SEQ ID NO 3; (b) a polypeptide having the amino acid sequence of SEQ ID NO 6; and (c) any of the isolated nucleic acid sequences described above. Within a particularly preferred embodiment, a cDNA sequence encoding a simian ETF polypeptide is provided that has a 483-bp 5' noncoding region preceding an open reading same of 486 bp (489 bp if the stop codon is included) and a 306-bp 3' noncoding region. Also provided is a cDNA sequence encoding a human ETF polypeptide which has a 316-bp 5' noncoding region preceding an open reading frame of 486 bp and a 400-bp 3' noncoding region. The nucleotide sequences and deduced amino acid sequences of simian and human open reading frames are disclosed in SEQ ED NOS 1 and 4, respectively. Both the simian and human open reading frames (SEQ ID NOS 2 and 5, respectively) encode a precursor polypeptide. The precursor polypeptides each comprise a 48-amino acid leader sequence, and are followed by the mature simian or human ETF polypeptides. Active simian and human ETF polypeptides are disclosed in SEQ ID NO 3 and 6, respectively.

Also provided by the present invention are isolated antibodies which specifically bind ETF (e.g. monoclonal or polyclonal antibodies), as well as hybridomas which produce monoclonal antibodies.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety as if each were individually noted for incorporation.

BRIEF DESCRIPTION OF THE DRAWINGS

FIG. 1 depicts the nucleotide sequence and deduced amino acid sequence of an active simian species of ETF nucleotides 145 to 486 of Sequence I.D. No. 1, and amino acids 1 to 114 of Sequence I.D. No. 3.

FIG. 2 depicts the nucleotide sequence and deduced amino acid sequence of an active human species of ETF nucleotides 145 to 486 of Sequence I.D. No. 4, and amino acids 1 to 114 of Sequence I.D. No. 6.

FIG. 3 depicts one representative purification and protein sequencing scheme useful in isolating ETF potypeptides.

FIG. 4 shows the homology between nucleotide sequences encoding a human (nucleotides 145 to 486 of Sequence I.D. No. 4) and a simian (nucleotides 145–486 of Sequence I.D. No. 1). species of ETF. The human sequence is shown above the simian sequence.

FIG. 5 shows the homology between a human and a simian species of ETF. The human sequence (Sequence I.D. No. 5) is shown above the simian sequence (Sequence I.D. No. 2) In both species, the leader sequence (amino acids 1 through 48) is cleaved from the precursor polypeptide to form the mature polypeptide (amino acids 49 through 162).

DETAILED DESCRIPTION OF THE INVENTION

Figure 6:
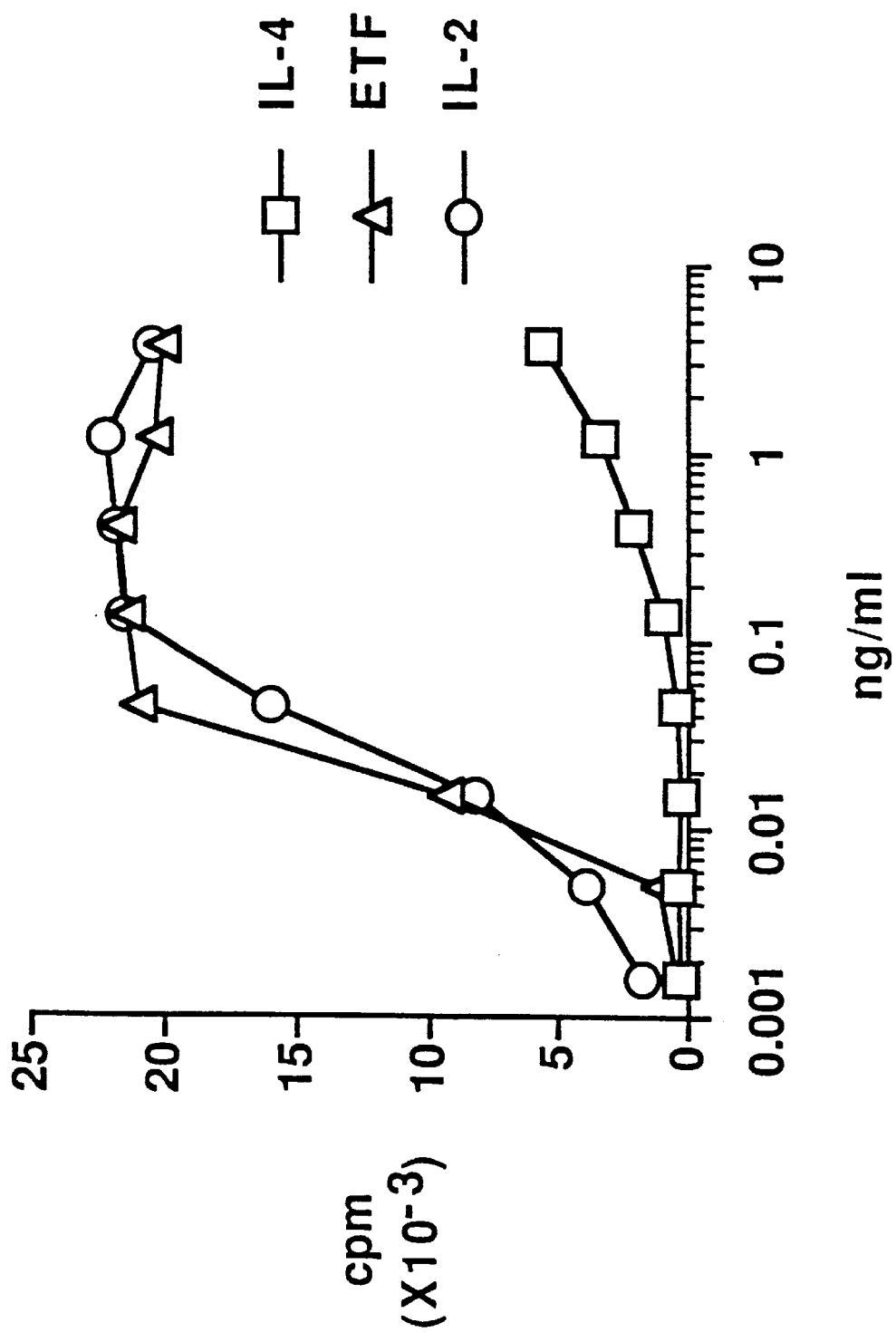
FIG. 6 is a graph that shows the biological activity of recombinant ETF, IL-2 and IL-4 in vitro using CTLL-2 cells. The in vitro proliferative response of CTLL-2 cells was measured at increasing concentrations of recombinant cytokine (expressed as ng/ml). The data are expressed as cpm of $^3$H-thymidine incorporated $(X10^{-3})$.

"Epithelium-derived T-cell factor" or "ETF" refers to mammalian polypeptides that are structurally similar to the polypeptides disclosed herein (including alletic variants) and that stimulate T-lymphocytes to proliferate and differentiate. ETF is distinguishable from IL-2, IL-4, IL-7, IL-9, IL-10, and IL-12 in structure and cellular origin (see Table 1). In primates, ETF polypeptide is initially produced by epithelial cells as a 162-amino acid precursor ETF polypeptide. This precursor contains a 48-amino acid leader sequence that is removed from the precursor polypeptide to form the mature polypeptide. The mature ETF polypeptide is capable of signaling proliferation and/or differentiation of precursor or mature T-cells. The protein, therefore, can be used to promote long-term in vitro culture of T-lymphocytes and T-cell lines.

TABLE 1

Origin and structure of T-cell growth factors

| FACTOR | SIZE (kDA) | NO. OF AMINO ACIDS* | SOURCE |
| --- | --- | --- | --- |
| IL-2 | 15 | 153 | Activated lymphocytes |
| IL-4 | 15–20 | 153 | Activated T-lymphocytes Bone marrow stromal cells Mast cells |
| IL-7 | 25 | 177 | Bone marrow and thymic stromal cells |
| IL-9 | 30–40 | 144 | Activated T-lymphocytes |
| IL-10 | 16–20 | 178 | Th2 lymphocytes |
| IL-12** | 40 and 35 | 328 and 253 | B-lymphoblastoid cell lines |
| ETF | 15–17 | 162 | Epithelial cells |

*Number in human polypeptides encoded by the open reading frame.
**Two glycoprotein subunits are necessary for activity.

"sETF" refers to a simian species of ETF. "hETF" refers to a human species of ETF. "rETF" refers to recombinant ETF. Both purified sETF and rETF will stimulate proliferation of CTLL-2 cells (Gillis and Smith, *Nature* 268:154 (1977); ATCC TIB 214). Briefly, in the CTLL-2 proliferation assays, supernatants of cells transfected with recombinantly expressed precursor and inframe fusions of mature forms of SETF induced CTLL-2 cell proliferation. For other assays, peripheral blood T-cells ("PBT") and peripheral blood mononuclear leukocytes ("PBL") were isolated from human peripheral blood. rETF was found to stimulate proliferation of PBT and PBL previously cultured with phytohemagglutinin ("PHA"). rETF also stimulated proliferation of PHA activated $CD4^+$, and $CD8^+$ cells. rETF stimulated proliferation of resting human T-cells or resting murine T-cell clones in the presence of anti-CD3 (T-cell receptor) antibodies. Experiments with PHA activated PBT demonstrate that rETF exerts its growth stimulatory effects independently of IL-2, in that antibodies to IL-2 or to the IL-2 receptor do not inhibit ETF.

The terms ETF, sETF and HETF include analogs or subunits of native mammalian polypeptides that are encoded by nucleotide sequences that hybridize, under moderate to high stringency conditions, to probes defined by nucleotides 145 through 486 of SEQ ID NOS 1 or 4 or to their complementary DNA or RNA strands, and that code on expression for polypeptides that stimulate proliferation and differentiation of T-lymphocytes, and stimulate proliferation of T-cell lines and isolated PBT.

"Recombinant DNA technology" or "recombinant", as used herein, refers to techniques and processes for producing specific polypeptides from microbial (e.g., bacterial, fungal or yeast) or mammalian cells or organisms (e.g., transgenics) that have been transformed or transfected with cloned or synthetic DNA sequences to enable biosynthesis of heterologous peptides. Native glycosylation patterns will only be achieved with mammalian cell expression systems. Yeast provide a distinctive glycosylation pattern. Prokaryotic cell expression (e.g., *E. coli*) will generally produce polypeptides without glycosylation.

"Biologically active" means that a particular mammalian ETF polypeptide is capable of stimulating T-lymphocyte proliferation and/or differentiation. In the case of sETF and hETF, this biological activity also corresponds to stimulation of the proliferation of murine or primate, for example, human, T-cell lines or PBT.

A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided in the form of an open reading frame uninterrupted by internal nontranslated sequences, or introns, that are typically present in eukaryotic genes. Sequences of non-translated DNA may be present 5' or 3' from an open reading frame, where the same do not interfere with manipulation or expression of the coding regions.

"Recombinant expression vector" refers to a plasmid comprising a transcriptional unit comprising an assembly of (1) a genetic element or elements having a regulatory role in gene expression, for example, promoters or enhancers, (2) a structural or coding sequence that encodes ETF biological activity, and if desired, (3) appropriate transcription and translation initiation and termination sequences. Representative examples of various regulatory elements that can be used are discussed below (see Recombinant DNA Techniques). Structural elements intended for use in yeast expression systems preferably include a leader sequence enabling exctracellular secretion of translated polypeptide by a yeast host cell. Alternatively, in a bacterial expression system, the recombinant polypeptide may include a N-terminal methionine residue. The N-terminal methionine residue may be subsequently cleaved from the expressed recombinant polypeptide to provide a product suitable for further purification.

"Recombinant microbial expression system" refers to a substantially homogeneous monoculture of suitable host microorganisms, for example, bacteria, such as *E. coil*, or yeast, such as *S. cerevisiae*, that have stably integrated a recombinant transcriptional unit into chromosomal DNA or carry the recombinant transcriptional unit as a component of a resident plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

Transformed host cells are cells that have been transformed or transfected with a recombinant expression vector. Expressed mammalian ETF will be located within the host cell and/or secreted into culture supernatant, depending upon the nature of the host cell and the gene construct inserted into the host cell.

Moderate stringency hybridization conditions, as defined herein and as known to those skilled in the art, refer to conditions described in, for example, Sarmibrook et al., supra, Vol. 2, pp. 8.46–8.49 and 9.47–9.55. Conditions of moderate stringency, as defined by Sambrook et al. include, for example, overnight hybridization and post-hybridization washes at 55° C., 5×SSC, 0.5% SDS. Severe or high stringency conditions include higher temperatures of hybridization and post-hybridization washes, or lower salt concentrations.

ETF Polypeptides

As described in more detail below, a simian species of ETF (sETF) has been purified, and the N-terminus sequenced. Using the N-terminal amino acid sequence and PCR, cDNA encoding sETF was isolated, and utilized to determine the nucleotide sequence and deduced amino acid sequence of mature sETF (FIG. 1), and the nucleotide sequence and deduced amino acid sequence of a precursor of sETF polypeptide (SEQ ID NO 1 and SEQ ID NO 2). Precursor ETF polypeptide sequence in the simian species comprises a mature active protein (SEQ ID NO 3) preceded by a 48-amino acid leader sequence. The leader sequence is amino acids 1–48 of SEQ ID NO 2. Primate ETF stimulates in a statistically significant manner the proliferation of murine T-cell lines (e.g., CTlL-2) and the proliferation and differentiation of human PBT cells.

The present invention also comprises other mammalian ETF, including human ETF, having ETF biological activity and encoded by nucleotide sequences that hybridize, under conditions of moderate to high stringency, to probes defined by SEQ ID NO 1, SEQ ID NO 4, and SEQ ID NO 12. A plasmid containing a recombinant clone of human ETF cDNA was deposited with the American Type Culture Collection, 12301 Parklawn Drive, Rockville, Md. 20852 USA ("ATCC") in accordance with the Budapest Treaty on the International Recognition of the Deposit of Microorganisms for the Purposes of Patent Procedure on Feb. 19, 1993 under accession number ATCC 69245. The deposit was named "I41-hETF" and comprised an *E. coli* strain containing plasmid hETF/pDC that contained a 316-bp 5' noncoding region preceding an open reading frame of 486 bp and a 400-bp 3' noncoding region flanked by the Sal I adapters shown in SEQ ID NOS 7 and 8. All restrictions on the availability to the public of the material deposited will be irrevocably removed upon the granting of a patent.

The amnino acid structure of ETF polypeptides disclosed herein may be modified by forming covalent or aggregative conjugates with other chemical moieties, such as glycosyl groups, lipids, phosphate, acetyl groups and the like, or by creating amino acid sequence mutants. Covalent derivatives of mammalian ETF are prepared by liking particular functional groups to mammalian ETF amino acid side chains or at the N-terminus or C-terminus of a mammalian ETF polypeptide. Other derivatives of mammalian ETF within the scope of this invention include covalent or aggregative conjugates of mammalian ETF or its fragments with other proteins or polypeptides, such as by synthesis in recombinant culture as N-terminal or C-terminal fusions. For example, the conjugated polypeptide may be a signal (or leader) polypeptide sequence at the N-terminal region of a mammalian ETF polypeptide for transport from its site of synthesis to a site inside or outside of the cell membrane or wall (e.g., the yeast α-factor leader). Further, using conventional techniques, ETF polypeptides can be expressed as polypeptide fusions comprising additional polypeptide sequences, such as Fc or other immunoglobulin sequences, linker sequences, or other sequences that facilitate purification and identification of ETF polypeptides. Still further, ETF polypeptide fusions can comprise fusions with other cytokines to provide novel polyfunctional entities. Other cytokines include, for example, any of interleukins-1 through 13, tumor necrosis factor (TNF), granulocyte macrophage-colony stimulating factor (GM-CSF), granulocyte-colony stimulating factor (G-CSF), mast cell growth factor (MGF) and other cytokines that affect immune cell growth, differentiation or function. Within a particularly preferred embodiment, ETF may be fused in frame to IL-2 (or a biologically active portion of IL-2) in order to provide an IL-2/ETF fusion protein.

The present invention further includes ETF polypeptides having altered glycosylation. Briefly, ETF polypeptides expressed in yeast or mammalian expression systems (e.g., COS-7 cells (ATCC CRL 1651)) may be similar or significantly different in molecular weight and glycosylation pattern than a native ETF polypeptide. This depends upon the choice of expression system. Expression of ETF polypeptides in bacterial expression systems, such as *E. coli*, provide non-glycosylated molecules.

Functional mutant analogs of human or other mammalian ETF can be synthesized, for example, with inactivated N-glycosylation sites by oligonucleotide synthesis and ligation or by site-specific mutagenesis techniques. ETF polypeptide derivatives can be expressed in homogeneous, reduced carbohydrate form using yeast expression systems N-glycosytation sites in eukaryotic polypeptides are characterized by an amino acid triplet Asn-Φ-Ω, where Φ is any amino acid except Pro and Ω is Ser or Thr. An ETF mutant derivative, as referred to herein, is a polypeptide substantially homologous to a sequence of a native mammalian ETF but that has an amino acid sequence different from a native mammalian ETF polypeptide because of a deletion, insertion or substitution.

Bioequivalent analogs of ETF polypeptides or ETF muteins may be constructed by making various substitutions of amino acid residues or sequences, or by deleting terminal or internal residues or sequences not needed for biological activity. For example, Cys residues can be deleted or replaced with other amino acids to prevent formation of incorrect intramolecular disulfide bridges upon renaturation. Other approaches to mutagenesis involve modification of dibasic amino acid residues to enhance expression in yeast systems in which KEX2 protease activity is present. Generally, substitutions are made conservatively by substituting an amino acid having physiochemical characteristics resembling those of the native residue.

Antisense or sense oligonucleotides comprise single-stranded nucleic acid sequences (either RNA or DNA) capable of binding to sense ETF mRNA or antisense ETF cDNA sequences. An antisense or sense oligonucleotide, according to the present invention, comprises a fragment of the nucleotide sequences in FIGS. 1 or 2 or a DNA or RNA complement of the nucleotide sequences in FIGS. 1 and 2. Such a fragment comprises at least about 14 nucleotides and is capable of binding to ETF DNA. The ability to create an antisense or a sense oligonucleotide, based upon a cDNA sequence for ETF is described in, for example, Stein and Cohen, *Cancer Res*. 48:2659 (1988), and van der Krol et al., *BioTechniques* 6:958 (1988).

Isolation and characterization of ETF from non-recombinant cellular sources requires a mammalian cell line that produces ETF and a responder cell line that proliferates in response to ETF stimulation. A biological assay for mammalian ETF may employ a growth factor-dependent T-cell line as a detector of factors that induce lymphoid cell proliferation. T-cells isolated from blood samples taken from humans or from other mammals also can be used to assay mammalian ETF polypeptides.

An ETF-dependent cell line can be derived from murine CTLL-2 cells. This cell line responds to purified human, murine, and recombinant IL-2 and murine IL-4 but not to IL-1, IL-3, human IL-4, or any of the other known growth factors.

One can utilize the simian or human ETF cDNA sequences disclosed herein to obtain cDNAs encoding other mammalian homologs of simian or human ETF by cross-species hybridization techniques. Briefly, an oligonucleotide probe may be created based upon the nucleotide sequence of the protein coding region of sETF cDNA as described in FIG. 1 or SEQ ID NO 1 or hETF cDNA as described in FIG. 2 or SEQ ID NO 4. This probe can be made by standard techniques, such as those described in Sambrook et al. supra.

The simian or human probe is used to screen a mammalian cDNA library or genomic DNA library under moderate stringency conditions. Mammalian cDNA libraries can be made from mRNAs isolated from, for example, murine peripheral blood lymphocytes. Alternatively, other cDNA libraries or mRNAs isolated from various tissues or cell lines can be screened by Northern hybridization to determine a suitable source of mammalian ETF DNA or MRNA.

CV-1/EBNA ETF Purification

As described in more detail below, ETF has been purified from a non-homogeneous protein solution, such as conditioned medium collected from cells expressing ETF, to provide an isolated polypeptide preparation. ETF activity in crude conditioned medium samples is not always detectable using currently available ETF bioassay techniques. At least one purification step is typically required before ETF biological activity is detectable utilizing bioassay techniques described herein.

A non-homogeneous protein solution, e.g., conditioned medium, is prepared by growing the CV-1/EBNA line (C. J. McMahan et al., EMO J., 10(10):2821–2832 (1991); ATCC CRL 10478) of African Green Monkey kidney cells in a tissue culture medium. Preferably, the medium is high glucose Dulbecco's Modified Essential Medium ("DMEM", Gibco, Grand Island, N.Y.). Most preferably, a growth medium and a production medium are used. The growth medium employed in isolating sETF as described herein was high glucose (4500 mg/L) DMEM supplemented with 7.5% fetal bovine serum, 50 u/ml penicillin, 50 ug/nml streptomycin, 3 to 4.0 mM L-glutamine, 1 mM sodium pyruvate, 0.1 mM non-essential amino acids and 10 mnM N-[2-hydroxyethyl]piperazine-N'-[2-ethanesulfonic acid] ("HEPES") buffer. A serum free production medium of DNEM without phenol red supplemented with 50 u/ml penicillin, 50 ug/ml streptomycin, 3 to 4.0 mM L-glutamine, 1 mM sodium pyruvate, 0.1 mM non-essential amino acids and 10 mM HEPES buffer was developed for ETF production and purification. The CV-1/EBNA cells were attachment dependent and could be grown in dishes, flasks, roller bottles or microcarriers.

More specifically, ETF was produced by culturing CV-1/EBNA cells on microcarriers in a controlled bioreactor. Cell stocks were maintained in roller bottle flasks. To start a production cycle, cells were trypsinized and inoculated into a spinner flask containing the growth medium described above and 5 g/l Cytodex® 3 microcarriers (Pharmacia). initial seeding density ranged from 1.5 to $3.5 \times 10^5$ cells/ml. To ensure efficient cell attachment to the microcarriers, the cells were kept in the spinner flask for 2 to 24 hours. Spinner flask cultures were incubated at 37° C. and agitated at 25 to 40 RPM. After the attachment period, the culture was transferred to a controlled bioreactor. Bioreactor temperature, pH, oxygen and agitation set points were 37° C., 7.0, 20% saturation (relative to air), and 75–85 RPM, respectively. For routine observation of cell growth and health, samples were observed by bright field microscopy. Quantification of cell growth was achieved by counting released nuclei after treatment with a solution of 100 mM citric acid and 0.1% crystal violet.

The culture was supplemented with additional growth medium when ammonia levels reached 5.0 mM. This was repeated until the microcarriers were confluent. The culture medium was then exchanged to the serum-free production medium described above. This procedure was accomplished by allowing the microcarriers to settle to the bottom of the reactor, aspirating the growth medium and replacing it with production medium. This was repeated until an approximately 3,125 fold dilution was achieved. Two to six rounds of production can be expected. In each round, cells were allowed to produce for four to seven days after which 80% of the production medium was collected. This was repeated until the cells were completely detached from the microcarriers.

Approximately 64 liters of CV-1/EBNA conditioned media were used to purify and provide protein for the N-terminal amino acid sequence of sETF. As shown in FIG. 3, the purification scheme included ultrafiltration, hydrophobic chromatography, anion exchange chromatography, reverse-phase high performance liquid chromatography (RP-BPLC), and sodium dodecyl sulfate polyacrylamide gel electrophoresis (SDS-PAGE). Protein was sequenced by electro blotting proteins from the SDS gel to a polyvinylidene fluoride ("PVDF") membrane and determining an N-terminal amino acid sequence by Edman degradation directly from the PVDF membrane. N-terminal amino acid sequencing revealed the first 33 amino acids shown in SEQ ID NO 3. Subsequent sequencing of a cDNA clone obtained from a CV-1/EBNA cDNA library produced a DNA sequence encoding the polypeptide of SEQ ID NO 2. This clone includes a 48 amino acid leader sequence from SEQ ID NO 2 and a mature polypeptide represented by SEQ ID NO 3.

Recombinant DNA Techniques

Human, simian and other mammalian ETF polypeptides are preferably produced by recombinant DNA techniques. Generally, such techniques involve insertion of cDNA encoding a human or other mammalian ETF polypeptide or a derivative thereof into an expression vector, transfecting or transforming a host cell with the expression vector, and culturing the cell under conditions which promote expression of the ETF polypeptide.

Briefly, recombinant production of mammalian ETF polypeptides or derivatives thereof first requires isolation of a DNA clone (i.e., cDNA) that codes on expression for a mammalian ETF polypeptide or a derivative thereof CDNA clones are derived from primary cells or cell lines that express mammalian ETF polypeptides. First total cell mRNA is isolated, then a cDNA library is made from the mRNA by reverse transcription. A cDNA clone may be isolated and identified using the DNA sequence information provided herein to design a cross-species hybridization probe or PCR primer as described below.

The isolated cDNA is preferably in the form of an open reading frame uninterrupted by internal nontranslated sequences, or introns. Genomic DNA containing the relevant nucleotide sequences that code for expression of mammalian ETF polypeptides can also be used as a source of genetic information useful in constructing coding sequences. The isolated cDNA can be mutated by techniques known in the art to promote ETF derivatives or analogs that exhibit ETF biological activity.

Recombinant expression vectors include synthetic or cDNA-derived nucleic acid fragments encoding ETF or biologically active derivatives thereof. The nucleic acid fragment which encodes ETF or a derivative thereof is operably linked to a suitable transcriptional or translational regulatory or structural nucleotide sequence, such as one derived from mammalian, microbial, viral, insect, or plant genes. Examples of regulatory sequences include, for example, a genetic sequence having a regulatory role in gene expression (e.g., transcriptional promoters or enhancers), an optional operator sequence to control transcription, a sequence encoding suitable mRNA ribosomal binding sites, and appropriate sequences that control transcription and translation initiation and termination. Nucleotide sequences are operably linked when the regulatory sequence functionally relates to the structural gene. For example, a DNA sequence for a signal peptide (secretory leader) may be operably linked to a structural gene DNA sequence for a mammalian ETF or derivative thereof if the signal peptide is expressed as part of a precursor amino acid sequence and participates in the secretion of a mammalian ETF. Further, a promoter nucleotide sequence is operably linked to a coding sequence (e.g., structural gene DNA) if the promoter nucleotide sequence controls the transcription of the structural gene nucleotide sequence. Still further, a ribosome binding site may be operably linked to a structural gene nucleotide coding sequence (e.g., mammalian ETF) if the ribosome binding site is positioned within the vector to encourage translation.

Suitable host cells for expression of mammalian ETF or derivatives thereof include prokaryotes, yeast or higher eukaryotic cells under the control of appropriate promoters. Prokaryotes include gram negative or gram positive organisms, for example $E.\ coli$ or bacilli. Suitable prokaryotic hosts cells for transformation include, for example, $E.\ coli, Bacllus\ subtilis, Salmonella\ typhimurium$, and various other species within the genera Pseudomonas, Streptomyces, and Staphylococcus. As discussed in greater detail below, examples of suitable host cells also include yeast such as $S.\ cerevisiae$, a mammalian cell line such as Chinese Hamster Ovary (CHO) cells, or insect cells. Cell-free translation systems could also be employed to produce mammalian ETF or derivatives thereof using RNAs derived from the DNA constructs disclosed herein. Appropriate cloning and expression vectors for use with bacterial, fungal, yeast, and mammalian cellular hosts are described, for example, in Pouwels et al. *Cloning Vectors: A Laboratory Manual*, Elsevier, New York, 1985.

When a mammalian ETF or derivative thereof is expressed in a yeast host cell, the nucleotide sequence (e.g., structural gene) that codes on expression for a mammalian ETF or derivative thereof may include a leader sequence. The leader sequence may enable improved extracellular secretion of translated polypeptide by a yeast host cell.

Mammalian ETF may be expressed in yeast host cells, preferably from the Saccharomyces genus (e.g., $S.\ cerevisiae$). Other genera of yeast, such as Pichia or Kluyveromyces, may also be employed. Yeast vectors will often contain an origin of replication sequence from a $2\mu$ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in HItzeman, EP-A-73,657.

Yeast vectors can be assembled, for example, using DNA sequences from pBR322 for selection and replication in $E.\ coli$ ($Amp^r$ gene and origin of replication). Other yeast DNA sequences that can be included in a yeast expression construct include a glucose-repressible ADH2 promoter and α-factor secretion leader. The ADH2 promoter has been described by Russell et al- (*J. Biol. Chem.* 258:2674, 1982) and Beier et al. (*Nature* 300:724, 1982). The yeast a-factor leader sequence directs secretion of heterologous polypeptides. The α-factor leader sequence is often inserted between the promoter sequence and the structural gene sequence. See, e.g., Kuijan et al., *Cell* 30:933, 1982; and Bitter et al., *Proc. Natl. Acd. Sci. USA* 81:5330, 1984. A leader sequence may be modified near its 3' end to contain one or more restriction sites. This will facilitate fusion of the leader sequence to the structural gene.

Yeast transformation protocols are known to those skilled in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Depression of the ADH2 promoter occurs when glucose is exhausted from the medium.

Alternatively, in a prokaryotic host cell, such as $E.\ coli$, the mammalian ETF or derivative thereof may include an N-terminal methionine residue to facilitate expression of the recombinant polypeptide in a prokaryotic host cell. The N-terminal Met may be cleaved from the expressed recombinant mammalian ETF.

The recombinant expression vectors carrying the recombinant mammalian ETF structural gene nucleotide sequence or derivative thereof are transfected or transformed into a suitable host microorganism or mammalian cell line.

Expression vectors transfected into prokaryotic host cells generally comprise one or more phenotypic selectable markers. A phenotypic selectable marker is, for example, a gene encoding proteins that confer antibiotic resistance or that supply an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a mamnualian ETF structural gene sequence. Other commercially available vectors include, for example, pKK223-3 (Pharrnacia Fine Chemicals, Uppsala, Sweden) and pGEM1 (Promega Biotec, Madison, Wis., USA).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EPA 36,776) and tac promoter (Sambrook et al., *Molecular Cloning: A Laboratory Manual*, Cold Spring Harbor Laboratory, (1989)). A particularly useful prokaryotic host cell expression system employs a phage λ $P_L$ promoter and a cI857ts thermolabile repressor sequence. Plasmid vectors available from the American Type Culture Collection that incorporate derivatives of the λ $P_L$ promoter include plasmid pHUB2 (resident in *E. coli* strain JME9 (ATCC 37092)) and pPLc28 (resident in *E. coli* RR1 (ATCC 53082)).

Mammalian or insect host cell culture systems can also be employed to express recombinant mammalian ETF polypeptide or derivatives thereof. Examples of suitable mammalian host cell lines include the COS-7 lines of monkey kidney cells (Gluzman et al., *Cell* 23:175, (1981); ATCC CRL 1651), L cells, C127 cells, 3T3 cells (ATCC CCL 163), CHO cells, HeLa cells (ATCC CCL 2), and BHK (ATCC CRL 10) cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences in mammalian host cell expression vectors may be provided by viral sources. For example, commonly used mammalian cell promoter sequences and enhancer sequences are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Vial early and late promoters are particularly useful because both are easily obtained from a viral genome as a fragment that may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included Exemplary mammalian expression vectors can be constructed as disclosed by Okayama and Berg (*Mol. Cell. Biol.* 3:280, 1983). Additional useful mammalian expression vectors are described in U.S. patent application Ser. No. 07/480, 694 filed Feb. 14, 1990 and U.S. Pat. No. 5,350,683.

Purification of Recombinant Mammalian ETF

Within one aspect of the present invention, ETF polypeptides may be prepared by culturing transformed host cells under culture conditions necessary to express mammalian ETF polypeptides or derivatives thereof. The resulting expressed polypeptides may then be purified from culture media or cell extracts. A mammalian ETF polypeptide or derivative thereof may be concentrated using a commercially available protein concentration filter, for example, an Amicon or Millipore Pellicon ultrafiltration unit. With or without the concentration step, the culture media can be applied to a purification matrix such as a hydrophobic chromatography medium. Phenyl Sepharose® CL-4B (Pharmacia) is the preferred medium. Alternatively, an anion exchange resin can be employed, for example, a matrix or substrate having pendant diethylaminoethyl (DEAE) groups. The matrices can be acrylarnide, agarose, dextran, cellulose or other types commonly employed in protein purification. Alternatively, gel filtration medium can be used.

Finally, one or more reverse-phase high performance liquid chromatography (RP-HPLC) steps employing hydrophobic RP-HPLC media, e.g., silica gel having pendant methyl or other aliphatic groups, can be employed to further purify ETF. Some or all of the foregoing purification steps, in various combinations, can also be employed to provide a substantially homogeneous recombinant protein.

Alternatively, some or all of the steps used in the purification procedure described above for simian ETE can also be employed.

Recombinant protein produced in bacterial culture is usually isolated by initial disruption of the host cells, centrifugation, extraction from cell pellets if an insoluble polypeptide, or from the supernatant if a soluble polypeptide, followed by one or more concentration, salting-out, ion exchange or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express ETF as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reverse-phase HPLC steps for purification of recombinant human IL-2 on a preparative HPLC column.

Preparation of Antibodies Against ETF

Within one aspect of the present invention, ETF, including derivatives thereof, as well as portions or fragments of these proteins such as the ETF peptides, may be utilized to prepare antibodies which specifically bind to ETF. Within the context of the present invention the term "antibodies" should be understood to include polyclonal antibodies, monoclonal antibodies, fragments thereof such as F(ab')$_2$ and Fab fragments, as well as recombinantly produced binding partners. Antibodies are defined to be specifically binding if they bind to the ETF with a $K_a$ of greater than or equal to about $10^7$ M$^{-1}$. The affinity of a monoclonal antibody or binding partner may be readily determined by one of ordinary skill in the art (see Scatchard, *Ann. N.Y. Acad. Sci.* 51:660–672, 1949).

Polyclonal antibodies may be readily generated by one of ordinary skill in the art from a variety of warm-blooded animals such as horses, cows, goats, sheep, dogs, chickens, rabbits, mice, or rats, given the disclosure provided herein. Briefly, ETF is utilized to immnunize the animal through intraperitoneal, intramuscular, intraocular, or subcutaneous injections. The immunogenicity of a ETF or ETF peptide may be increased through the use of an adjuvant such as Freund's complete or incomplete adjuvant. Following several booster inmmunizations, small samples of serum are collected and tested for reactivity to the ETF. A variety of assays may be utilized in order to detect antibodies which specifically bind to a ETF. Exemplary assays are described in detail in *Antibodies: A Laboratory Manual* Harlow and Lane (eds.), Cold Spring Harbor Laboratory Press, 1988. Representative examples of such assays include: Countercurrent Immuno-Electrophoresis (CIEP), Radioimrnunoassays, Radioimmunoprecipitations, Enzyme-Linked Immuno-Sorbent Assays (ELISA), Dot Blot assays, and sandwich assays (see U.S. Pat. Nos. 4,376, 110 and 4,486,530; see also *Antibodies: A Laboratory Manual*, supra). Particularly preferred polyclonal antisera will give a signal that is at least three times greater than background. Once the titer of the animal has reached a plateau in terms of its reactivity to the ETF, larger quantities of polyclonal antisera may be readily obtained either by weekly bleedings, or by exsanguinating the animal.

Monoclonal antibodies may also be readily generated using well-known techniques (see U.S. Pat. Nos. RE 32,011, 4,902,614, 4,543,439, and 4,411,993; see also *Monoclonal Antibodies, Hyhridomas: A New Dimension in Biological*

*Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, within one embodiment a subject animal such as a rat or mouse is injected with a form of ETF suitable for generating an immune response against the ETF. Representative examples of suitable forms include, among others, cells which express ETF, or peptides which are based upon the ETF sequence. Additionally, many techniques are known in the art for increasing the resultant immune response, for example, by coupling ETF or ETF peptides to another protein such as ovalbumin or keyhole limpet hemocyanin (KLM), or through the use of adjuvants such as Freund's complete or incomplete adjuvant. The initial immunization may be through intraperitoneal, intramuscular, intraocular, or subcutaneous routes.

Between one and three weeks after the initial immunization the animal may be reimmunized with another booster immunization. The animal may then be test bled and the serum tested for binding to the ETF using assays as described above. Additional immunizations may also be accomplished until the animal has plateaued in its reactivity to the ETF. The animal may then be given a final boost of ETF or ETF peptide, and three to four days later sacrificed. At this time, the spleen and lymph nodes may be harvested and disrupted into a single cell suspension by passing the organs through a mesh screen or by rupturing the spleen or lymph node membranes which encapsidate the cells. Within one embodiment the red cells are subsequently lysed by the addition of a hypotonic solution, followed by imunediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the ETF that is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein-Barr virus (BV) (see Glaskry and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Maryland (see Catalogue of *Cell Lines & Hybridomas*, 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63—Ag 8.653 (ATCC No. CRL 1580), which may be utilized for fusions with either mouse, rat, or human cell lines. Fusion between the myeloma cell line and the cells from the immunized animal may be accomplished by a variety of methods, including the use of polyethylene glycol (PEG) (see *Antibodies: A Laboratory Manual*, Harlow and Lane (eds.), Cold Spring Harbor Laboratory Press, 1988) or electrofusion (see Zimmerman and Vienken, *J. Membrane Biol.* 67:165–182, 1982).

Following fusion, the cells are placed into culture plates containing a suitable medium, such as RPMI 1640 or DMEM (Dulbecco's Modified Eagles Medium) (JRH Biosciences, Lenexa, Kans.). The medium may also contain additional ingredients, such as Fetal Bovine Serum ("FBS," ie., from Hyclone, Logan, Utah, or JRH Biosciences), thymocytes which were harvested from a baby animal of the same species as was used for immunization, or agar to solidify the medium. Additionally, the medium should contain a reagent which selectively allows for the growth of fused spleen and myeloma cells. Particularly preferred is the use of HAT (hypoxanthine, aminopterin, and thymidine) (Sigma Chemical Co., St. Louis, Mo.). After about seven days, the resulting fused cells or hybridomas may be screened in order to determine the presence of antibodies which recognize the ETF. Following several clonal dilutions and reassays, a hybridoma producing antibodies which bind to ETF may be isolated.

Such hybridomas may be utilized to produce large quantities of monoclonal antibody, either by injecting the hybridoma cells intraperitoneally into syngeneic mice to produce ascitic fluid containing the monoclonal antibodies, or by in vitro culture in flasks or roller bottles.

Other techniques may also be utilized to construct monoclonal antibodies (see Huse et al., "Generation of a Large Combinational Library of the Irmmunoglobulin Repertoire in Phage Lambda," *Science* 246:1275–1281, December 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, August 1989; see also Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population and utilized to create heavy and light chain immunoglobulin cDNA expression libraries in the kIMMUNOZAP(H) and kIMMUNOZAP(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. The construction of these proteins may be readily accomplished by one of ordinary skill in the art (see Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmann etal., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyrme Activity," *Science* 239:1534–1536, 1988; Chaudhary et al., "A Recombinant Immunotoxin Consisting of Two Antibody Variable Domains Fused to Pseudomonas Exotoxin," *Nature*

339:394–397, 1989; see also, U.S. Pat. No. 5,132,405 entitled "Biosynthetic Antibody Binding Sites"), given the disclosure provided herein. Briefly, within one embodiment, DNA molecules encoding ETF-specific antigen binding domains are amplified from hybridomas which produce a specifically binding monoclonal antibody, and inserted directly into the genome of a cell which produces human antibodies (see Verhoeyen et al., supra;, see also Reichinann et al., supra). This technique allows the antigen-binding site of a specifically binding mouse or rat monoclonal antibody to be transferred into a human antibody. Such antibodies are preferable for therapeutic use in humans because they are not as antigenic as rat or mouse antibodies.

Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or ETF binding domain of the antibody may be found in the variable region of the antibody. Furthermore, DNA sequences which encode smaller portions of the antibody or variable regions which specifically bind to mammalian ETF may also be utilized within the context of the present invention. These portions may be readily tested for binding specificity to the ETF utilizing assays described below.

Within a preferred embodiment, genes which encode the variable region from a hybridoma producing a monoclonal antibody of interest are amplified using oligonucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{Hl}$, $V_L$ and $C_L$ regions. These primers may be utilized to amplify heavy or light chain variable regions, which may then be inserted into vectors such as IMMUNOZAP*(H) or IMMUNOZAP*(L) (Stratacyte), respectively. These vectors may then be introduced into E. coli for expression. Utilizing these techniques, large amounts of a single-chain protein containing a fusion of the $V_H$ and $V_L$ domains may be produced (see Bird et al., Science 242:423426, 1988).

Other "antibodies" which may also be prepared utilizing the disclosure provided herein, and thus which are also deemed to fall within the scope of the present invention include humanized antibodies (e.g., U.S. Pat. No. 4,816,567 and WO 94/10332), microbodies (e.g., WO 94/09817) and transgenic antibodies (e.g., GB 2 272 440).

Once suitable antibodies have been obtained, they may be isolated or purified by many techniques well known to those of ordinary skill in the art (see Antibodies: A Laboratory Mamal, supra). Suitable techniques include ammonium sulfate precipitation, peptide or protein affinity columns, HPLC or RP-HPLC, purification on protein A or protein G columns, or any combination of these techniques. Within the context of the present invention, the term "isolated" as used to define antibodies means "substantially free of other blood components."

Antibodies of the present invention have many uses. For example, within one aspect of the invention antibodies may be utilized in order to detect the presence of ETF in a sample, such as a biological fluid. For example, within one embodiment immobilized anti-ETF antibody may be incubated with a sample (e.g. a biological sample such as serum) suspected of containing ETF, under conditions and for a time sufficient to permit binding of the immobilized antibody to ETF. Several washings may then be accomplished in order to remove non-binding constituents, followed by the addition of a labeled antibody which also recognizes ETF. After several additional washing steps, detection of the labeled antibody may be accomplished in order to determine the presence of ETF in the original sample. Representative examples of suitable labels, as well as methods for conjugating or coupling antibodies to such labels are described in more detail below.

Antibodies of the present invention may also be coupled or conjugated to a variety of other compounds for either diagnostic or therapeutic use. Such compounds include, for example, toxic molecules, molecules which are nontoxic but which become toxic upon exposure to a second compound, and radionuclides. Representative examples of such molecules are described in more detail below.

Antibodies which are to be utilized therapeutically are preferably provided in a therapeutic composition comprising the antibody and a physiologically acceptable carrier or diluent. Suitable carriers or diluents include, among others, neutral buffered saline or saline, and may also include additional excipients or stabilizers such as buffers, sugars such as glucose, sucrose, or dextrose, chelating agents such as EDTA, and various preservatives.

LABELS

The nucleic acid molecules, ETF polypeptides, and antibodies of the present invention may be labeled or conjugated (either through covalent or non-covalent means) to a variety of labels or other molecules, including for example, fluorescent markers, enzyme markers, toxic molecules, molecules which are nontoxic but which become toxic upon exposure to a second compound, and radionuclides.

Representative examples of fluorescent labels suitable for use within the present invention include, for example, Fluorescein Isothiocyanate (FITC), Rodamine, Texas Red, Luciferase and Phycoerythrin (PE). Representative examples of enzyme markers or labels include alkaline phosphatase, horseradish peroxidase, and β-galactosidase. Representative examples of toxic molecules include ricin, abrin, diphtheria toxin, cholera toxin, gelonin, pokeweed antiviral protein, tritin, Shigella toxin, and Pseudomonas exotoxin A Representative examples of molecules which are nontoxic, but which become toxic upon exposure to a second compound include thymnidine kinases such as HSVTK and VZVTK. Representative examples of radionuclides include Cu64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212.

As will be evident to one of skill in the art given the disclosure provided herein, the above described nucleic acid molecules, ETF polypeptides, and antibodies may also be labeled with other molecules such as colloidal gold, as well either member of a high affinity binding pair (e.g., avidin-biotin).

DIAGNOSTIC USE OF ETF SEQUENCES

Within another aspect of the present invention, probes and primers are provided for detecting ETF. Within one embodiment of the invention, probes are provided which are capable of hybridizing to ETF DNA or RTNA For purposes of the present invention, probes are "capable of hybridizing" to ETF DNA if they hybridize to Sequence I.D. Nos. 1 or 4 (or their complementary sequences) under conditions of moderate or high stringency (see Sambrook et al., supra).

Probes of the present invention may be composed of either deoxyribonucleic acids (DNA) ribonucleic acids (RNA), nucleic acid analogues, or any combination of these, and may be as few as about 12 nucleotides in length, usually about 14 to 18 nucleotides in length, and possibly as large as the entire sequence of the ETF.

Probes may be constructed and labeled using techniques which are well known in the art. Shorter probes of, for example, 12 or 14 bases may be generated synthetically. Longer probes of about 75 bases are preferably generated by, for example, PCR amplification in the presence of labeled precursors such as $^{32}$P-dCTP, digoxigenin-dUTP, or biotin-dATP.

Probes may be labeled by a variety of markers, including, for example, radioactive markers, fluorescent markers, enzymatic markers, and chromogenic markers. The use of $^{32}$P is particularly preferred for marking or labeling a particular probe.

Probes of the present invention may also be utilized to detect the presence of a ETF MnRNA or DNA within a sample. However, if ETF in RNA or DNA is present in only a limited amount, or if it is desired to detect a selected mutant sequence which is present in only a limited number, or if it is desired to clone ETF from a selected warm-blooded animal, then it may be beneficial to amplify the relevant sequence such that it may be more readily detected or obtained.

A variety of methods may be utilized in order to amplify a selected sequence, including, for example, RNA amplification (see Lizardi et al., Bio/Technolog 6:1197–1202, 1988; Kramer et al., Nature 339:401–402, 1989; Lomeli et al., Clinical Chem. 35(9): 1826–1831, 1989; U.S. Pat. No. 4,786,600), and DNA amplification utilizing Polymerase Chain Reaction ("PCR") (see U.S. Pat. Nos. 4,683,195, 4,683,202, and 4,800,159) (see also, U.S. Pat. Nos. 4,876, 187, and 5,011,769, which describe an alternative detection/amplification system comprising the use of scissile linkages).

Within a particularly preferred embodiment, PCR amplification is utilized to detect or obtain a ETF DNA Briefly, as described in greater detail below, a DNA sample is denatured at 95° C. in order to generate single stranded DNA Specific primers, as discussed below, are then annealed at 37° C. to 70° C., depending on the proportion of AT/GC in the primers. The primers are extended at 72° C. with Taq polymerase in order to generate the opposite strand to the template. These steps constitute one cycle, which may be repeated in order to amplify the selected sequence.

Primers for the amplification of a selected sequence should be selected from sequences which are highly specific and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and may be easily synthesized using techniques well known in the art.

Administration of Mamnmalian ETF Polvpeptide and Derivative Compositions

The present invention provides methods of using therapeutic compositions comprising an effective amount of ETF or nucleic acids which encode ETF in a suitable diluent or carrier. For therapeutic use, purified ETF or a biologically active derivative thereof, or nucleic acids which encode ETF, may be administered to a patient, preferably a human, for treatment in a manner appropriate to the indication. Representative examples of suitable routes for administration include intravenous injection or infusion, subcutaneous injection, inhalation, parenteral or intraperitoneal infusion, via a sustained release implant, transdermally, intra-nasally, intra-ocularly, mucosally, rectally and topically. Typically, an ETF therapeutic agent will be administered in the form of a pharmaceutical composition comprising purified polypeptide in conjunction with physiologically acceptable carriers, excipients or diluents. Such carriers will be nontoxic to patients at the dosages and concentrations employed. Ordinarily, the preparation of such compositions entails combining a mammalian ETF polypeptide or derivative thereof with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

Within one aspect of the present invention, methods are provided for treating or preventing gastrointestinal diseases, comprising the step of administering to a patient a therapeutically or prophylactically effective amount of ETF. Briefly, a wide variety of diseases are associated with disruption of the gastrointestinal epithelium or villi, including chemotherapy- and radiation-therapy-induced enteritis (i.e., gut toxicity) and mucositis, peptic ulcer disease, gastroenteritis and colitis, villus atrophic disorders, malignancy, and inflammatory bowel disease.

For example, chemotherapeutic agents and radiation therapy used in bone marrow transplantation and cancer therapy affect rapidly proliferating cells in both the hematopoietic tissues and small intestine, leading to severe and often dose-limiting toxicities. Damage to the small intestine mucosal barrier results in serious complications of bleeding and sepsis due to gastrointestinal flora entering the blood. Colony stimulating factors that promote proliferation of hematopoietic cells have allowed dose-intensification in chemotherapy and therefore gut toxicity has emerged as a potential dose limiting toxicity. A growth factor such as ETF that promotes proliferation and/or protection of the gastrointestinal epithelium therefore may be utilized to increase the tolerated doses for radiation therapy and chemotherapy agents which are dose limited by gastrointestinal toxicity (e.g., 5-fluorouracil (5-FU), high dose VP-16, or topetecan).

Effective treatment of gastrointestinal diseases may be determined by several criteria, including an enteritis score (based upon a composite score of clinical symptoms such as abdominal pain, cramping, stool guaiac and diarrhea), as well as related endpoints such as percent chemotherapy dose delivered, days of hospitalization, transfusions, intravenous fluid therapy, antimotility agents, ability to eat and quality of life.

Within another aspect of the present invention, methods are provided for treating HIV and HIV-associated diseases, comprising administering to a patient a therapeutically effective amount of ETF. Briefly, as noted above, ETF has been shown to stimulate both $CD4^+$ and $CD8^+$ cells, and therefore, may be administered (with or without additional therapies such as an antiretroviral therapy regimen) to a patient in order to positively effect the course of disease. Effective treatment of HIV and HIV-associated diseases may be determined by several criteria, including for A,example $CD4^+$ cell count, progression of disease and quantitation of HIV.

Biologically active ETF may likewise be utilized to treat a variety of other diseases or conditions wherein it is desired to stimulate proliferation of T-lymphocytes; to stimulate the proliferation of B lymphocytes, the secretion of immunoglobulin by B lymphocytes, or the secretion of γ-Interferon ("IFN") or TNF-α by B lymphocytes; to augment anti-infectious disease immunity; to induce CTL, LAK or NK lytic activity; or to augment the destruction of tumor cells or cells infected with virus.

It should be understood that the specific dose level for any particular patient may depend upon a variety of factors, including the activity of the specific compound administered, the age, body weight, general health, sex, diet, time of administration, route of administration, rate of excretion, drug combination and the severity of the particular disease being treated or prevented. Preliminary doses can be determined according to animal tests, and the scaling of dosages for human administration can be performed according to art-accepted practices Keeping the above description in mind, typical dosages of ETF may range from about 10 ug per square meter to about 10 mg per square meter. A preferred dose range is on the order of about 100 ug per square meter to about 300 ug per square meter.

The following examples are for purposes of illustration and not by way of limitation. Briefly, as shown in the examples below, ETF induces CTLL-2 proliferation, B cell proliferation, CTL, LAK, and NK killing activity and stimulates the secretion of immunoglobulins, γ-IFN and TNF-α. Accordingly, ETF can be used to augment the destruction of tumor cells or viral-infected cells and to augment anti-infectious disease immunity. In addition, ETF stimulates intestinal epithelial cells and protects against radio- and chemotherapy- induced gut toxicity. Unlike IL-2, administration of ETF in a mouse model did not cause toxicity related to vascular permeability.

EXAMPLE 1

PURIFICATION AND SEQUENCING FOR NATIVE sETF

Ultrafiltration

Ultrafiltration was not absolutely necessary to purify ETF. The procedure, however, does remove certain smaller contaminating proteins and reduces the volume, thus speeding up the purification scheme. The ultrafiltration step can be performed using either a YM10 or YM30 spiral cartridge, a hollow fiber cartridge, or a disc membrane in various types of ultrafiltration apparatus. An Amicon ultrafiltration system with a YM30 spiral cartridge, however, was preferred. No buffer exchange was required before or after this step.

A non-homogeneous protein solution, i.e. conditioned medium was obtained by growing CV-1/EBNA cell cultures in serum free, phenol red free DMEM in bioreactors with 5 g/l Cytodex® 3 microcarriers. 8×8 liter bioreactors (total of about 64 liters) were harvested, centrifuged to remove cells and microcarriers, filtered through a 0.22 micron cellulose acetate membrane filter, and then concentrated to a final volume of about two liters using a YM30 spiral cartridge. Preferably, the YM30 concentrate is filtered before undergoing hydrophobic chromatography. This step will minimize contamination by removing bacteria and other particulates. Any filter having a pore size from 0.1 to 0.45 microns that does not bind protein may be used; however, a 0.22 micron cellulose acetate membrane filter was preferred.

Hydrophobic Chromatoeraphy

Hydrophobic chromatography provided a quick way of transferring the protein into a low salt buffer that could be applied to anion exchange columns. In addition, it provided three to six fold purification. Still further, no buffer exchange was required before or after this step. Various hydrophobic columns are suitable. A Phenyl Sepharose® CL-4B column (Pharmnacia) was preferred. As an alternative to the hydrophobic chromatography step described herein, a diafiltration or dialysis step can be used.

Preferably, ammonium sulfate was added to the ultrafiltration concentrate to a final concentration of about 0.2 M. The ultrafiltration concentrate was buffered with 1 M BEPES at about pH 8.5 to a final concentration of about 20 mM. The concentrate was then pumped onto a Phenyl Sepharose® CL-4B column and washed with 0.2 M ammonium sulfate, 10 mM HEPES at about pH 8.5 to remove unbound protein. Bound proteins were eluted with 10 mM HEPES at about pH 8.5. The eluted protein peak (including ETF) was applied to an anion exchange column.

Anion Exchange Chromatographv

Anion exchange chromatography purification allowed additional purification without requiring dialysis or buffer exchange. This step preferably involved two passages of the Phenyl Sepharose® protein pool over columns containing an anion exchange media. After each passage, the bound proteins were eluted with NaCl in HEPES. Although various anion exchange media and buffer systems having a pH of about 8 to about 9 were suitable, DEAE Sephacel® (Pharmacia) followed by Mono Q allowed sequential anion exchange steps without buffer exchanges or dialysis. DEAE Sephacel® provided removal of some contaminating proteins prior to higher resolution Mono Q fast protein liquid chromatography ("FPLC," Pharnacia). The NaCl concentration used depended on the anion exchanger selected and the pH of the buffer chosen. Other salts could be substituted for the NaCl to elute the protein from the anion exchange gel.

Most preferably, NaCl was added to the Phenyl Sepharose pool to a final conductivity of about 1.2 mnilliSiemens/centimeter ("mS/cm") (less than approximately 0.1 M NaCl) and pumped onto a DEAE Sephacel® column that was equilibrated with about 0.1 M NaCl in about 10 mM HEPES at about pH 8.5. Bound proteins were eluted with a linear gradient from about 0.1 to about 0.3 M NaCl in about 10 mM HEPES at about pH 8.5. The active fractions (including ETF) were pooled for application to a Mono Q anion exchange column.

The active DEAE Sephacel® pool was diluted with about 10 mM HEPES to a final conductivity less than 1.6 mS/cm (less than 0.14 M NaCl). The diluted pool was then pumped onto a Mono Q FPLC column that was equilibrated with about 0.14 M NaCl in about 10 mM HEPES at about pH 8.5. Bound proteins were eluted with a gradient from about 0.14 M to about 0.5 M NaCl in about 10 mM IEPES at about pH 8.5. The active fractions (including ETF) were pooled for reverse-phase high performance liquid chromatography (RP-HPLC).

RP-HPLC

The native mammalian ETF polypeptide is stable from approximately pH 7 to approximately pH 9 and at approximately pH 2.5 in 0.1% trifluoroacetic acid ("TFA") with various amounts of acetonitrile ("AcN"). The ETF activity was not recovered when acidic aqueous buffers were used, thus not allowing cation exchange chromatography to be included in the purification scheme. C4 RP-HPLC columns (Vydac™ 0.46=25 cm, 5 micron) provided the greatest purification. Other reverse-phase columns (C8 or C18) did not work; the protein eluted from C4 at a high AcN concentration and was not recovered from C8 or C18 at all. Other buffer systems that were tried (e.g., ammonium acetate/methanol pH 7) were not successful.

The RP-HPLC purification preferably involved two passages of the Mono Q active pool over the Vydac™ C4 matrix. In the first passage, the Mono Q active pool was pumped onto a C4 HPLC column at about 1 ml/min and eluted with a gradient of 0.1% TFA/H₂O to 0.1% TFA/100% AcN at the following gradient:

0 to 45% AcN, 1% AcN/mininute
45 to 60% AcN, 0.5% AcN/minute
60 to 100% AcN, 2% AcN/minute Peak active fractions (including ETF) elute between about 48 and about 51% AcN. Active fractions determined by bioassay were pooled, diluted with 0.1% TFA/H₂O to reduce AcN concentration, and applied to the same C4 column.

The active, diluted pool from the C4 TFA/AcN run was pumped back on to the C4 column, washed with 0.1% TFA/H₂O and eluted with a linear gradient of 0.1% TFA/H₂O (buffer A) to 0.1% TFA/60% n-propanol (buffer B) at about 0.5 ml/min. The gradient was run at about 0.5% buffer Birnin. Fractions were bioassayed to identify the ETF-containing fractions. Em-containing fractions were pooled.

SDS-PAGE

Purified ETF can be visualized by silver stained SDS-PAGE. Purified mammalian ETF protein bands isolated by SDS-PAGE may be electroblotted and analyzed to determine their N-terminal amino acid sequences. The ETF protein band can be identified by bioassay.

Aliquots of purified ETF protein fractions from the C4 TFA/n-propanol BPLC run were evaporated to dryness in a vacuum centrifuge, resuspended in non-reducing SDS sample buffer and run on a polyacrylamide SDS gel. Preferably, TPLC purified ETF was run on SDS-PAGE (Phastgel® 8–25%, Pharrnacia) in two adjacent lanes. Prior to fixing and staining, approximately 1 mm slices of gel were cut from one lane of the Phastgel® and put directly into bioassays. The remaining gel was developed and the silver stained bands matched with slices put into bioassays. The ETF activity corresponded to the 15–17 kDa portion of the gel. For specific activity determination, purified ETF was resuspended in reducing SDS sample buffer, run on 14% polyacrylamide SDS gel (Novex) and silver stained. The purity of the sETF polypeptides corresponding to 15–17 kDa was approximately 222,000 times greater than the sETF polypeptide purity in the CV-1/EBNA conditioned media at the beginning of the purification scheme (Table 2). In addition to purity and protein data, Table 2 shows the activity of the native sETF polypeptide in a CTLL-2 bioassay (described below in Example 2) conducted after each step of the purification process.

PVDF Blot

Purified ETF protein fractions from the foregoing RP-HPLC step were run on a 14% polyacrylamide SDS gel, and blotted to a PVDF membrane (ProBlot® from Applied Biosystems) at about a 60 V setting for about one hour. Protein bands were visualized by staining the PVDF membrane with Coomassie blue (0.1% in 10% acetic acid, 50% methanol). The membrane may be destained using the same solution without the Coomassie blue stain to highlight the protein bands. The 15–17 kDa protein band corresponding to the ETF activity was cut out and N-terminal protein sequence determination was performed directly from the PVDF membrane.

sETF Polyleptide Sequencing

The N-terminus of the 15–17 kDa polypeptide, blotted onto a PVDF membrane, was sequenced by Edman degradation in an Applied Biosystems protein sequencer. The results indicated the identity of the first 33 amino acids shown in SEQ ID NO 3. Subsequent sequencing of a cDNA clone obtained from a simian library provided a sequence encoding the polypeptide of SEQ ID NO 2. The polypeptide of SEQ ID NO 2 comprises a 48 amino acid leader sequence and a mature polypeptide represented by SEQ ID NO 3.

TABLE 2

Monkey ETF from CV-1/EBNA cell-conditioned serum free media[1]

| SAMPLE | VOLUME | PROTEIN CONC. UG/ML | TOTAL PROTEIN | ACTIVITY UNITS/ML[2] | TOTAL ACTIVITY UNITS | SPECIFIC ACTIVITY UNITS/UG | FOLD PURIFICATION |
|---|---|---|---|---|---|---|---|
| Crude | 64 L | 40–70 | 3.2 g | <100 | | (1.0) | 1 |
| Phenyl Seph SM | 1.7 L | 2100 | 3.6 g | 3000 | 5,100,000 | 1.4 | 1.4 |
| DEAE SM | 364 ml | 1300 | 473 mg | 5100 | 1,900,000 | 3.9 | 3.9 |
| Mono Q SM | 215 ml | 310 | 66.65 mg | 7664 | 1,650,000 | 24.8 | 25 |
| HPLC TFA-AcN SM | 14 ml | ND[3] | ND | 70546 | 987,644 | ND | ND |
| HPLC TFA-prop SM | 4 ml | ND | ND | 220,000 | 880,000 | ND | ND |
| TFA-prop peak | 2 ml | (88) | (176 ug) | 440,000 | 888,000 | (5045) | (5000) |
| SDS PAGE band | | | (4 ug) | | | (222,000) | (222,000) |

[1]Values in parenthesis are estimates from silver stained SDS PAGE. Other protein values were determined by Biorad Microprotein Assay (BSA standard)
[2]Activity was determined by CTLL-2 bioassay
[3]ND = not determined

EXAMPLE 2

BIOASSAY

CTLL-2 cells provide a fast and sensitive bioassay for detection of ETF polypeptides. Other cell lines that also proliferate in response to ETF with varying sensitivity are CTLL-2.4 (Valentine et al., Eur J. Immunol., 21(4):913 (1991)), 32D (Greenberger, Federation Proceedings 42:2762 (1983)), BAF-BO3 (Hatalkeyama et al., Cell, 59:837 (1989)), MO7e (Avanzi et al., Br. J Haematol. 69:359 (1988)), and TFI (Kitamura et al., J. Cell. Physciol., 140:323 (1989)).

Preferably, CTLL-2 cells are grown in high glucose DMEIM supplemented with about 30 ng/ml IL-2, 5% fetal bovine serum (FBS), $5\times10^{-5}$ M 2-mercaptoethanol, 50 U/ml penicillin, 50 ug/ml streptomycin, and 3–4.0 mM L-glutamine at 37° C., 10% $CO_2$ and 97% humidity. CTLL-2 is a factor dependent cell line requiring IL-2 for growth. Consequently, for assay, CTLL-2 cells are washed twice with high glucose DNMM supplemented with 5% FBS, $5\times10^{-5}$ M 2-mercaptoethanol, 50 U/ml penicillin, 50 ug/ml streptomycin, 3–4.0 mM L-glutamine to remove IL-2. ETF samples to be assayed are titrated with high glucose DMEM supplemented with 5% FBS, $5\times10^{-5}$ M 2-mercaptoethanol, 50 U/ml penicillin, 50 ug/ml streptomycin, 3–4.0 mM L-glutamine in 96 well flat-bottomed microtiter plates. Washed CTLL-2 cells are added (final assay volume 100 μl, 2000 cells/well) and the plates incubated about 24 hours at 37° C. and 10% $CO_2$. The plates are pulsed with $^3$H-thymidine (25Ci/mMole) at 0.5 μCi/well for about 5 hours, then harvested (Inotech 96 well cell harvester) and cpm counted (Packard Matrix 96 gas proportional counting system). Units are calculated from cpm where 1 unit equals the number of microliters that gives 50% maximal stimulation.

EXAMPLE 3

PREPARATION OF sETF cDNA CLONE

The sequence of the N-terminal 31 amino acids of purified sETF polypeptide (amino acids 1–31 in SEQ ED NO 3) was used to design synthetic oligonucleotide primers for PCR amplification of ETF-specific DNA sequences. The first six amino acids of the N-terminus (Asn-Trp-Val-Asn-Val-Ile) were used to design one primer, a degenerate mixture coding for all possible codon usages of the first six amino acid residues:

5'-AAYTGGGTNAAYGTNATH-3' (Sequence I.D. No. 9)

as shown in SEQ ID NO 9 where Y is T or C; His A, T, or C; and N is A, C, G, or T. The amino acid sequences of the simian mature N-terminus 26–31 (Tyr-Thr-Glu-Ser-Asp-Val) were used to design a second primer, a degenerate mixture coding for a complement of all possible codon usages of amino acids 26–31 omitting position 3 of Val:

5'-ACRTCNGAYTCNGTRTA-3' (Sequence I.D. No. 10). and

5'-ACRTCRCTYTCNGTRTA-3' (Sequence I.D. No. 11)

as shown in SEQ ID NOS 10 and 11, respectively, where Y and N are as defined above and R is A or G.

Polyadenylated RNAs from CV-1/EBNA cells stimulated for 24 hr, 37 hr, and 72 hr with 10 ng/ml phorbol 12-myristate 13-acetate ("PiMA") were used as separate templates for first strand cDNA synthesis. A portion of first strand reactions was added to commercially available PCR reaction mixes containing the oligonucleotide primers. This mixture was subjected to 31 cycles of PCR amplification in 100 μl reactions in standard buffer with the primers at 1 μM concentration. The cycles were programmed as follows: denaturation at 94° C. for 0.5 min., annealing step for 0.5 min, and elongation step at 72° C. for 0.75 min. Two cycles of annealing at each of 55° C., 53° C., and 51° C. were followed by 25 cycles with an annealing temperature of 49° C.

Following amplification, samples were purified and subjected to agarose gel electrophoresis. This yielded a 92 base pair DNA fragment that was excised from gel lanes from two separate reactions involving CV-1/EBNA cells. The 92 base pair DNA fragment was purified using an Elutip-D column (Schleicher & Schuefl, Keene NH), cloned into pBluescript SK⁻(Stratagene, La Jolla, Calif.) and used for dideoxy DNA sequencing.

A hybridization probe was prepared by random prime labeling of the subcloned 92 base pair DNA fragment. The hybridization probe was used to screen a portion of a plasmid library containing cDNA inserts prepared from CV-1/EBNA polyadenylated RNA This resulted in the isolation of clone C85.sETF that has an open reading frame comprising the nucleotide sequence shown in SEQ ID NO 1.

The nucleotide sequence of the polypeptide coding region of sETF is illustrated in SEQ ID NO 1. This sequence was derived from insert C85.sETF that was Sal I Tinkered into the Sal I site of expression vector pDC406 (C. J. McMahan et al., *EMBO J.*, 10(10):2821–2832 (1991)). Polyadenylated mRNA was prepared from a CV-1/EBNA cell line and cDNAs were prepared using standard techniques. The CV-1/EBNA line is a producer of sETF. cDNA ends were adapted with Sal I adapters (Haymerle et al., *Nucleic Acid Res*, 14:8615–24 (1986)):

5'-TCGACTGGAACGAGACGACCTGCT-3' (Sequence I.D. No. 7)

3'-GACCTTGCTCTGCTGGACGA-5' (Sequence I.D. No. 8)

(SEQ ID NOS 7 and 8, respectively) and cloned into vector pDC406. A pool consisting of approximately 500 individual plasmid-containing isolates was plated and screened by hybridization to a DNA probe fragment. The DNA probe fragment was prepared using PCR amplification of sETF sequences from CV-1/EBNA cell line cDNA.

EXAMPLE 4

CLONING HUMAN ETF

A sETF probe was prepared from an isolated, purified and radiolabeled Sal I fragment (about 1.37 kb) containing sETF cDNA by random prime labeling. The specific activity of the probe was approximately $1 \times 10^6$ cpm/ng. On Northern blots, the probe was hybridized to human RNAs from various sources, including a IMTLH cell line. The IMTLH cell line was derived from a stable transformation of a human bone marrow stromal cell culture with pSV3Neo. The probe was hybridized to human RNAs at about 42° C. in about 40% formamide for about 18 hours. Hybridization was followed by washing in 6×SSC for about ten minutes at 22° C. followed by washing in 2×SSC at 42° C. for about 30 minutes. Autoradiography revealed a positive signal in the IMTLH lane.

We probed Southern blots of Sal I-digested library pools of the IMTLH cDNA library to identify a pool containing a human ETF cDNA. Using the Haymerle et al., *Nucleic Acid Res*, 14:8615–24 (1986) method used above for the CV-1/EBNA library, the IMTLH library was constructed in expression vector pDC406 Pool "I41", a pool of approximately 1000 different cDNA clones, was identified as positive. Approximately 4000 colonies of "I41" then were plated and probed by conventional colony hybridization methods to identify a clone containing the human ETF cDNA. Only a single clone, I41.hETF, was shown to encode human ETF. There is approximately 96% nucleotide sequence identity and approximately 96% amino acid sequence identity between human and simian ETF open reading frae sequences (FIGS. 4 and 5).

The human ETF cDNA was used as a probe for Northern blot analysis of simian and human RNAs. Northern analysis of a variety of human tissues indicated that ETF mRNA is expressed by many tissues, most abundantly by placenta and skeletal muscle. Significant levels of ETF mRNA were also observed in other tissues including kidney, lung, liver, and heart. The best sources of ETF mRNA so far observed have been adherent mononuclear cells (monocyte enriched, PBM) and epithelial and fibroblast cell lines such as CV-1/EBNA and IMTLH. Freshly isolated uncultured PBL also express very low levels of ETF mRNA. Activated peripheral blood T cells, a rich source of IL-2 and IFN-ganima mRNA, express no detectable ETF mRNA nor do B lyphoblastoid cell lines such as MP1.

EXAMPLE 5 rETF STIMULATION OF CTLL-2 PROLIFERATION cDNAs encoding mature forms of ETF (nucleotides 145 to 486, inclusive, in SEQ ID NOS 1 and 4) were inserted downstream of a heterologous mammalian secretion signal to create rETF expression plasmid for sETF and hETF. The secretion signal is a largely hydrophobic stretch of amino acids (usually at the N-terminus of a polypeptide) that directs secretion and cleavage of the polypeptide between the C-terminus of the signal peptide and the N-terminus of the mature secreted protein (von Heijne, *Eur. J. Biochem.*, 116:419 (1981)). The secretion signal sequence used was a murine IL-7 signal sequence. The created plasrmids were transfected into COS-7 cells. Supernatants of the transfected cell cultures stimulated CTLL-2 proliferation. In addition, the coding region for the precursor form of hETF (SEQ ID NO 3) was inserted into pDC406 and transfected into CV-1/EBNA cells. Supernatants from cells transfected with pDC406:hETF, but not those transfected with empty vector, stimulated CTLL-2 proliferation. In addition, the coding region for the precursor form of hETF (SEQ ID NO 3) was inserted into pDC406 and transfected into CV-1/EBNA cells. Supernatants from cells transfected with pDC406:hETF (ie., hETF/pDC406), but not those transfected with empty vector, stimulated CTLL-2 proliferation.

EXAMPLE 6

INDUCTION OF CTLL-2 PROLIFERATION BY PURIFIED rETF

Recombinant simian ETF (simian rETF) was purified from supernatant of yeast expressing the sETF cDNA by a modification of the purification method described above in Example 1 in which the untafiltration and ion exchange steps were omitted. The purified simian rETF was compared to purified recombinant IL-2 and IL4 for biological activity. The purity of each of the three proteins was confirmed by amino acid analysis. Each of the three purified recombinant proteins was assayed for biological activity in vitro using CTLL-2 cells. CTLL-2 cultures contained the indicated cytokine with 2000 cells/culture in 100 μl of supplemented culture medium. The CTLL-2 cultures were pulsed with 0.5 μCi [$^3$H]thymidinelculture for the last 4 hours of a 24 hour culture period, harvested onto glass fiber filter and radioactivity was determined by avalanche gas ionization. The in vitro proliferative response of CTLL-2 cells was measured at increasing concentrations of recombinant cytokine (expressed as ng/ml). The data are expressed as cpm of 3H-thymidine incorporated (X10$^{-3}$) in FIG. 6.

EXAMPLE 7

INDUCTION OF B CELLS BY rETF

Human tonsillar B cells were purified as described by Armitage et al., in *J. Immunol.*, 150:3671–3680 (1993). The purified tonsillar B cells (1×10$^5$/well) were cultured in RPMI 1640 medium containing 10% fetal calf serum for three days in the presence of various concentrations of IL-2 or ETF in the presence or absence of 5μg/ml immobilized anti-human IgM or 5ng/ml phorbol myristate acetate (PMA). One μCi [$^3$H]thymidine/culture was added for the final 16 hours of culture. The results are expressed in Table 3 as the mean cpm of $^3$H-thymidine incorporated in triplicate cultures. The data show that IL-2 and ETF stimulation of B cell proliferation is increased when the cells are co-cultured with anti-IgM or tumor-promoting phorbol diesters such PMA.

In a second experiment, human tonsillar B cells were purified as described by Armitage et al., in *J. Immunol.*, 150:3671–3680 (1993). The purified tonsillar B cells were cultured in RPMI 1640 medium containing 10% fetal calf serum for 8 days with soluble human CD40 ligand (CD40L; 1:40 dilution of 10×concentrated COS s/n) and various concentrations of human IL-2 or human ETF. Secreted human immunoglobulin (Ig) isotypes were detected by ELISA as described by Armitage et al., in *J. Immunol.*, 150:3671–3680 (1993). The results are expressed in Table 4 as the mean of triplicate cultures. The data show that, in the presence of CD40L, ETF induces secretion of IgK IgG and IgA in a manner comparable to that seen with IL-2.

The data in these two experiments show that IL-2 and ETF eubit comparable B cell stimulatory activity. Based on these data one of ordinary skill in the art would expect that ETF would have T cell replacing factor (TRF) properties similar to IL-2 for B cell populations

TABLE 3

IL-2 and ETF Stimulation of B cells with and without anti-IgM or PMA.

| | cpm of $^3$H-thymidine incorporated | | |
|---|---|---|---|
| Addition | No co-stimulant | anti-IgM | PMA |
| Medium | 105 | 1008 | 2167 |
| IL-2 (100 ng/ml) | 447 | 13,234 | 9494 |
| IL-2 (10 ng/ml) | 322 | 11,007 | 7844 |
| IL-2 (1 ng/ml) | 182 | 6327 | 4694 |
| IL-2 (0.1 ng/ml) | 128 | 2171 | 3172 |
| ETF (100 ng/ml) | 343 | 11,005 | 8121 |
| ETF (10 ng/ml) | 221 | 8679 | 5437 |
| ETF (1 ng/ml) | 150 | 3223 | 3009 |
| ETF (0.1 ng/ml) | 130 | 956 | 2036 |

TABLE 4

IL-2 and ETF costimulation of immunoglobulin secretion by B cells.

| | Ig isotype secreted (ng/ml ± SEM) | | |
|---|---|---|---|
| Addition + CD40L | IgM | IgG1 | IGA |
| Medium | 124 ± 20 | 142 ± 23 | 24 ± 11 |
| IL-2 (100 ng/ml) | 1876 ± 155 | 2267 ± 154 | 1148 ± 76 |
| IL-2 (10 ng/ml) | 1437 ± 67 | 1146 ± 48 | 433 ± 25 |
| IL-2 (1 ng/ml) | 376 ± 54 | 346 ± 32 | 96 ± 12 |
| ETF (100 ng/ml) | 1647 ± 132 | 2476 ± 112 | 1094 ± 145 |
| ETF (10 ng/ml) | 1198 ± 76 | 796 ± 98 | 387 ± 38 |
| ETF (1 ng/ml) | 456 ± 35 | 436 ± 33 | 64 ± 3 | stimulated with an antigen.

On the basis of the data in Example 7 hereof, one of ordinary skill in the art would expect ETF, either alone or in combination with IL-2 or CD40L, to stimulate the proliferation of B cells, increase antibody or immunoglobulin secretion, and thereby augment anti-infectious disease immunity in human and non-human mammalian patients. As described above in the section on Administration of the ETF polypeptide, an effective amount of ETF in a suitable diluent or carrier can be administered to patients in which increased B cell proliferation and antibody or immunoglobulin secretion is desired.

EXAMPLE 8

INDUCTION OF CTL, LAK, AND NK LYTIC ACTIVITY BY rETF

Antigen specific cytolytic T lymphocytes (CTL) were generated in vitro. Human peripheral blood mononuclear cells (PBL) from one donor (5×10$^5$/culture) were stimulated with irradiated PBL ($5 \times 10^5$/culture) from an allogeneic donor in cultures containing various concentrations of either IL-2 or human rETF, or no cytokine. Cultures were performed as described by M. B. Widmer et al. in *J. Exp. Med.*, 166:1447 (1987), harvested after 7 days, and assayed for cytolytic activity against $^{51}$Cr labeled targets derived from the original stimulating donor. The lysis assay contained various numbers of the responding PBL cultured with 1000 labeled targets in 200 μl of medium in V-bottomed wells, and supernatants were collected after 4 hours of incubation. Lytic units were calculated as the inverse of the fraction of the responding culture required to generate 50% of the maximum specific $^{51}$Cr release. The data for the cytokine-treated CTL are summarized in Table 5.

Lymphokine activated killer (LAK) cells were generated under identical culture conditions as the CTL described above except that the human PBL were not stimulated with irradiated PBL from an allogeneic donor. Instead, irradiated autologous PBL were substituted and cytolytic activity was measured against the Daudi lymphoblastoid cell line. For the LAK assay, lytic units were calculated as the inverse of the fraction of the responding culture required to generate 30% of the maximum specific $^{51}$Cr release. The data for the cytokine-treated LAK cells are summarized in Table 6.

Natural killer (NK) cells were isolated from whole human PBL isolated by antibody affinity to paramagnetic microspheres with MACS (Niltenyi Biotec, Sunnyvale Calif.) using monoclonal antibodies against CD16. The purified NK cells were cultured for 3 days and cytolytic activity was measured against the K562 leukemia cell line. For the NK assay, lytic units were calculated as the inverse of the fraction of the responding culture required to generate 30% of the maximum specific $^{51}$Cr release. The data for the cytokine-treated NK cells are summarized in Table 7.

TABLE 5

Induction of CTL lytic activity by ETF and IL-2.

| ng/ml Cytokine | Lytic Units | |
| --- | --- | --- |
| | IL-2 | ETF |
| 30 | 129.8 | 367.7 |
| 10 | 144.9 | 441.0 |
| 3 | 124.1 | 503.2 |
| 1 | 139.3 | 221.1 |
| none | 50.3 | 50.3 |

TABLE 6

Induction of LAK lytic activity of ETF and IL-2.

| ng/ml Cytokine | Lytic Units | |
| --- | --- | --- |
| | IL-2 | ETF |
| 30 | 204.0 | 185.2 |
| 10 | 72.3 | 181.4 |
| 3 | 18.5 | 111.7 |
| 1 | 5.4 | 74.4 |
| none | 4.1 | 4.1 |

TABLE 7

Induction of NK cell lytic activity by ETF and IL-2.

| ng/ml Cytokine | Lytic Units | |
| --- | --- | --- |
| | IL-2 | ETF |
| 100 | 196 | 299 |
| 33 | 318 | 318 |
| 11 | 318 | 227 |
| 3.7 | 249 | 112 |
| 1.2 | 111 | 25 |
| none | 4 | 4 |

Interferon (IN) and tumor necrosis factor (TNF) secretion by NK cells also was analyzed. Natural killer (NK) cells were isolated from whole human PBL by antibody affinity to paramagnetic microspheres with MACS using monoclonal antibodies against CD56. IL-2, ETF, IL-12 and phytohemaggluttinin (PHA) were added alone or in combinations to the NK cels and the amount of IFN and TNF secreted by the NK cells was determined by ELISA The IL-12 was added as a supernatant of COS cells transfected with the IL-12 cDNA Supernatants from control transfected COS cells had no activity in this assay. The IFN and TNF secretion results are Summarized in Table 8.

Due to the similarity in activity between IL-2 and ETF in Examples 6, 7 and 8 hereof, one of ordinary skill in the art would expect ETF to stimulate the activity of CTL, LAK and NK cells and expand the population of T and B cells that can destroy tumor cells and viral-infected cells in human and non-human mammalian patients. As described above in the section on Administration of the ETF polypeptide, an effective amount of ETF in a suitable diluent or carrier can be administered to patients with carcinomas, melanomas, sarcomas, leukemia or lymphomas, or patients infected with Herpetoviridae, including cytomegalovirus, Polyomaviridae, Retroviridae, including HIV, influenza virus, Hepadnaviridae, hepatitis A, hepatitis B, hepatitis C, hepatitis delta, or hepatitis D.

EXAMPLE 9

IN VIVO TUMOR THERAPY

ETF's ability to augment an anti-tumor response was assessed in vivo using P815 mastocytoma in syngeneic DBA/2 mice in three different experiments involving different modes of administration. The P815 tumor grows in an ascites form leading to the death of untreated mice in three to four weeks.

Figure 7:
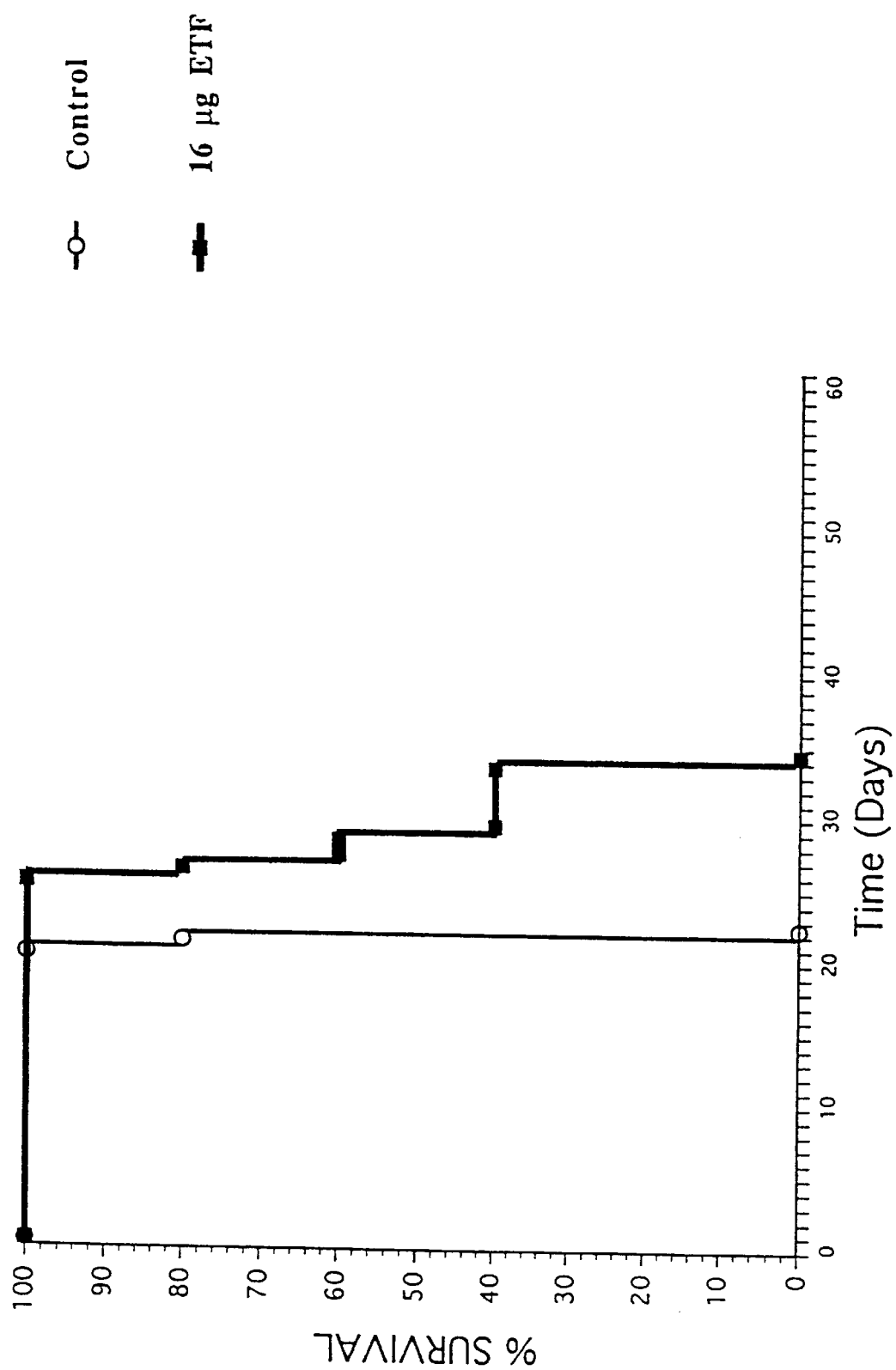
FIG. 7 is a graph that shows the ability of ETF in saline to augment an anti-tumor response in vivo of P815 mastocytoma in mice. Briefly, six- to ten-week old female DBA/2 mice received $2 \times 10^4$ syngeneic P815 tumor cells intraperitoneally. Half of the mice were treated once daily on days 10 and 24 post-tumor inoculation with 16 μg ETF in saline via intraperitoneal injections. The other half were used as controls and treated once daily on days 10 and 24 post-tumor inoculation with mouse serum albumin (MSA) via intraperitoneal injections.
Figure 8:
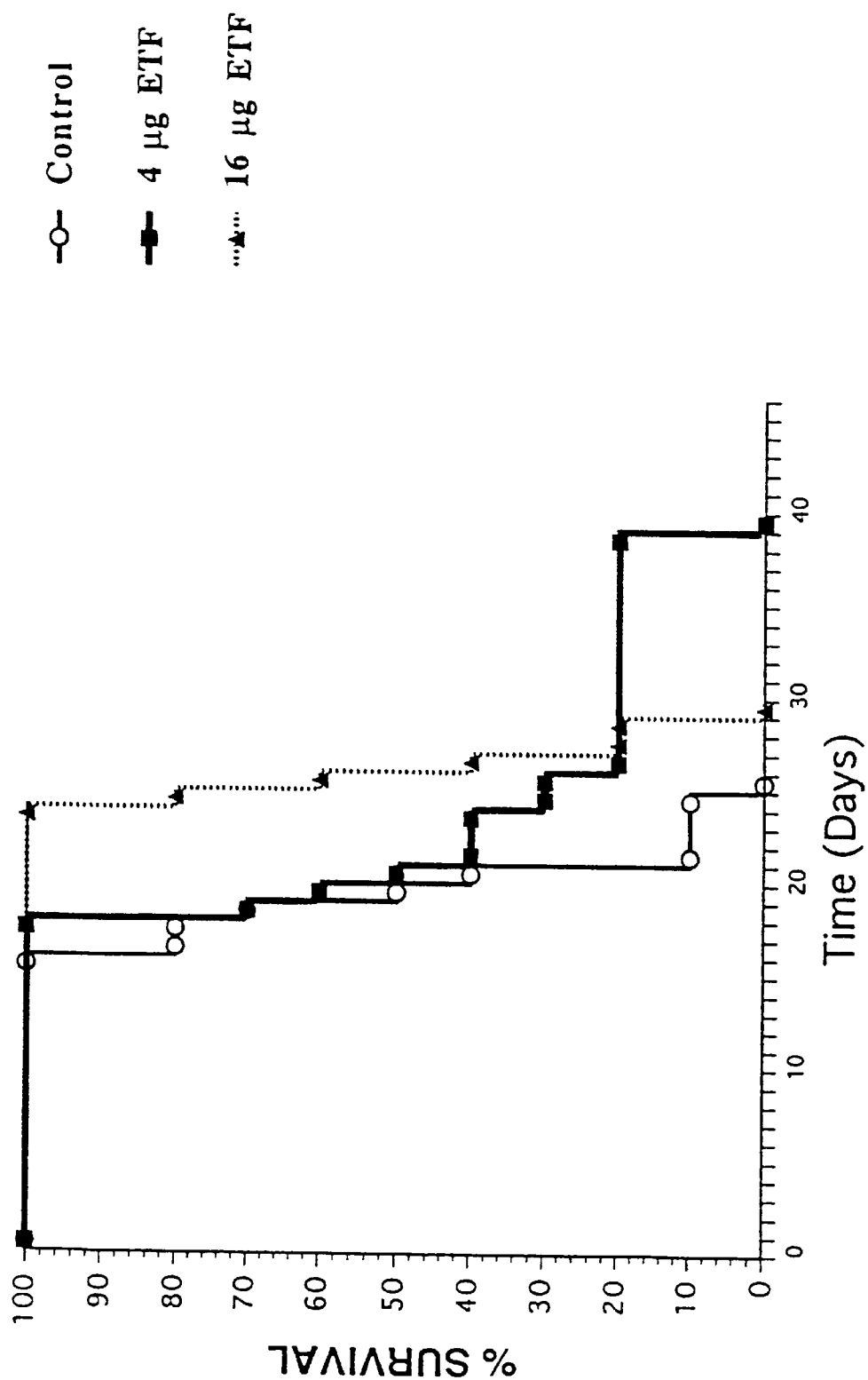
FIG. 8 is a graph that shows the ability of a single injection of ETF in glyceryl monooleate to augment an anti-tumor response in vivo against P815 mastocytoma in mice. Briefly, thirty 6- to 10-week old female DBA/2 mice received $2 \times 10^4$ syngeneic P815 tumor cells intraperitoneally. Ten days after tumor inoculation, two groups of ten mice received a single intraperitoneal injection of either 4 μg or 16 μg ETF in glyceryl monooleate. The remaining ten mice were used as controls and received a single intraperitoneal injection of glyceryl monooleate alone ten days after tumor inoculation.
Figure 9:
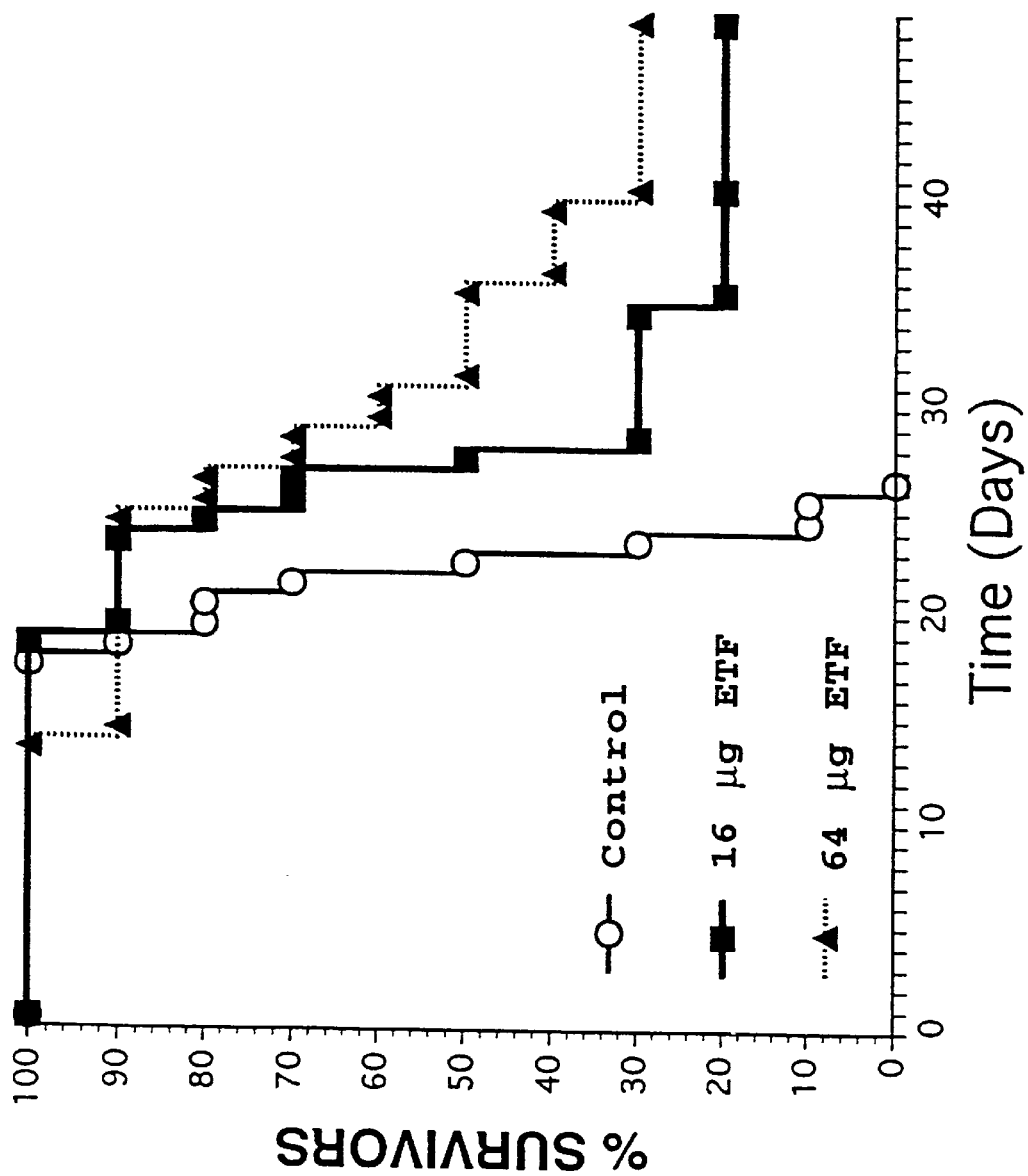
FIG. 9 is a graph that shows the ability of two injections of ETF in glyceryl monooleate to augment an anti-tumor response in vivo of P815 mastocytoma in mice. Briefly, thirty 6- to 10-week old female DBA/2 mice received $2 \times 10^4$ syngeneic P815 tumor cells intraperitoneally. Two groups of ten mice were treated once daily on days 10 and 16 post-tumor inoculation with either 16 μg or 64 μg ETF in glyceryl monooleate via intraperitoneal injections. The remaining ten mice were used as controls and treated once daily on days 10 and 16 post-tumor inoculation with glyceryl monooleate alone via intraperitoneal injections.

In the first experiment, ten 6- to 10-week old female DBA/2 mice received $2 \times 10^4$ syngeneic P815 tumor cells intraperitoneally. Five of the ten mice were treated once daily from day 10 to day 24 post-tumor inoculation with 16 μg ETF in saline via intraperitoneal injections. The other five mice were used as controls and treated once daily from day 10 to day 24 post-tumor inoculation with mouse serum albumin (MSA) via intraperitoneal injections. The experimental endpoint was survival to 60 days (the animals are considered cured) or death. As shown in FIG. 7, the controls all died between day 20 and day 22 post-tumor inoculation. The ETF-treated mice died between 25 and 34 day days post-tumor inoculation.

In the second and third experiment, ETF's short half life was compensated for by the use of a slow release system such as glyceryl monooleate (Myverol; Eastman Chemical Co., Kingsport, Tenn.). Glyceryl monooleate is a solid at room temperature and becomes an oil-like liquid at 37–40° C. When glyceryl monooleate comes into contact with a substance that is 35% water by weight, it forms a gel. Powdered recombinant ETF can be added to liquid glyceryl monooleate, mixed or shaken and injected into laboratory animals.

TABLE 8

Figure 10:
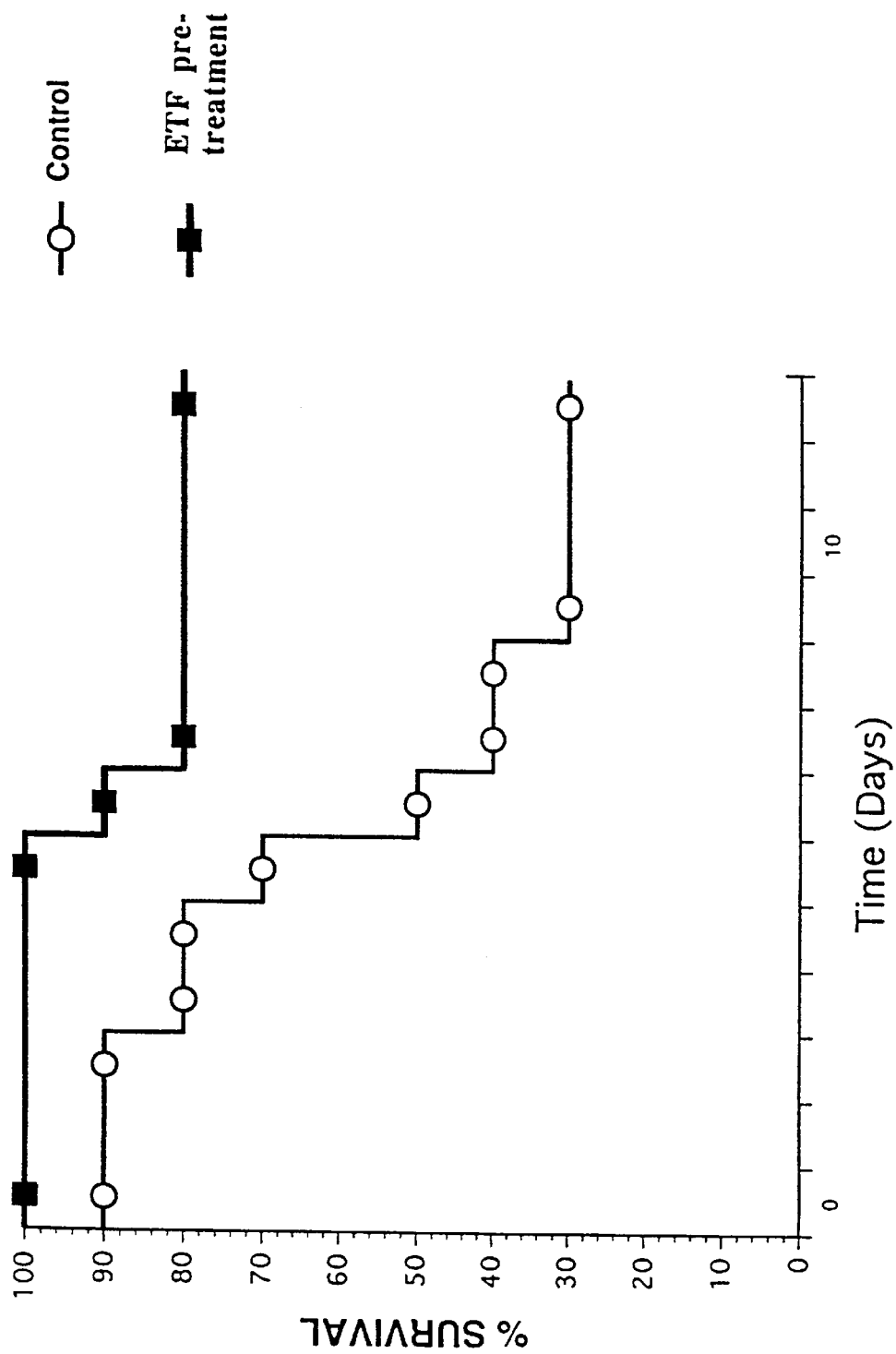
FIG. 10 is a graph that shows that pretreatment of ETF (4 μg bid) for three days protects mice from a lethal dose of doxorubicin hydrochloride (30 mg/kg $C_{27}H_{29}NO_{11}$. HCl).

IFN and TNF secretion by NK cells stimulated by IL-2, ETF, IL-12 or PHA.

| | Cytokine Secreted (pg/ml) | |
|---|---|---|
| Cytokine Additive | IFN | TNF |
| IL-2 (100 ng/ml) | 296 | 204 |
| IL-2 (10 ng/ml) | 179 | 126 |
| IL-15 (100 ng/ml) | 114 | 132 |
| IL-15 (10 ng/ml) | 0 | 32 |
| IL-12 (1/100) | 277 | 117 |
| IL-12 (1/1000) | 145 | 81 |
| IL-15 (100 ng/ml) + IL-12 (1/100) | 2029 | 942 |
| IL-2 (100 ng/ml) + IL-12 (1/100) | 2413 | 756 |
| PHA | 22 | 301 |
| none | 0 | 6 |

In the second experiment, thirty 6- to 10-week old female DBA/2 mice received $2\times10^4$ syngeneic P815 tumor cells intraperitoneally. Ten days after tumor inoculation, two groups of ten mice received a single intraperitoneal injection of either 4 μg or 16 μg ETF in glyceryl monooleate. The remaining ten mice were used as controls and received a single intraperitoneal injection of glyceryl monooleate alone ten days after tumor inoculation. Again the experimental endpoint was survival to 60 days or death. As shown in FIG. 8, the controls all died between day 15 and day 25 post-tumor inoculation. The mice that received a single injection of 4 μg ETF in glyceryl monooleate died between day 17 and day 34 post-tumor inoculation. The mice that received a single injection of 16 μg ETF in glyceryl monooleate died between day 23 and day 29 post-tumor inoculation.

In the third experiment, thirty 6- to 10-week old female DBA/2 mice received $2\times10^4$ syngeneic P815 tumor cells intraperitoneally. Two groups of ten mice were treated once daily on days 10 and 16 post-tumor inoculation with either 16 μg or 64 μg ETF in glyceryl monooleate via intraperitoneal injections. The remaining ten mice were used as controls and treated once daily on days 10 and 16 post-tumor inoculation with glyceryl monooleate alone via intraperitoneal injections. As shown in FIG. 9, the controls all died between day 17 and day 26 post-tumor inoculation. At day 26 post-tumor inoculation, 80% of the mice that received 64 μg ETF in glyceryl monooleate and 70% of the mice that received 16 μg ETF in glyceryl monooleate were still living. Twenty days later, at day 46 post-tumor inoculation, 30% of the mice that received 64 μg ETF in glyceryl monooleate and 20% of the mice that received 16 μg ETF in glyceryl monooleate were still living.

These three experiments show that ETF is able to augment an anti-tumor response in vivo. This effect may be due to a direct antitumor activity or indirectly through the stimulation of CTL, LAK, NK cells and T cells that can destroy tumor cells.

EXAMPLE 10

TOXICITY/VASCULAR PERMEABILITY AINALYSES

IL-2 toxicity has been linked to increased vascular permeability (Rosenberg et al., *JAMA*, 271(12):907–913 (1994)). In each of two experiments comparing the vascular permeability of controls and IL-2 and ETF treated mice, groups of C57B 116 mice (Charles River, Boston, Mass.) were treated with nine doses of IL-2 and ETF over a four-day period. In the first experiment, each group of mice consisted of 15 mice. In the second experiment, each group of mice consisted of 10–15 mice. In each experiment, a dose of 30 μg IL-2 or ETF were administered intraperitoneal (i.p.); for IL-2, 30 μg is 500,000 Cetus units. One hour before harvest on day 4, mice were treated with 0.5 μCi of iodinated albumin. The mice were sacrificed and their lungs were washed with 2 ml of saline, blotted, weighed and cpm counted. An aliquot of blood also was cpm counted to make sure that the amount of radioactivity injected was about the same in all mice. The data for both experiments are summarized below in Table 9. The data show that capillary leakage occurred when mice were treated with IL-2 but did not occur when mice were treated with ETF under the conditions described above

EXAMPLE 11

CHEMOTHERAPY INDUCED TOXICITY THERAPY

Murine intestinal epithelial (MIE) cells derived from murine fetal intestine explant cultures were used as responder cells in a ETF bioassay assay. To obtain the MIE cells, day 15 fetal intestine from C57B16 mice were harvested and minced. The tissue fragment were seeded into T25 flasks precoated with Matrigel Basement Membrane Matrix (Becton Dickinson Labware, Bedford, Mass.) and containing 10% fetal bovine serum (FBS)/D-Valine minimum essential medium (D-Valine NM at 780 mg/ml; Gibco). On day 3 or 4 of culture, the cells were transfected with SV40 large T antigen by exchanging approximately 30% of the culture medium with SV40 containing medium. After approximately, 48 hours, the cultures were fed with 10% FBS/D-Valine MEM with a 50% culture medium exchange. When the flasks were 75% confluent, the contents were removed with trypsin and subcloned to one 48-well plate in 10% FBSID-Valine MEM with 10 μ/ml of Fibronectin (Sigma Chemical Co., St. Louis, Mo.). Using Versene t5000 (Gibco) for all subsequent cell dissociations and the Fibronecin containing culture medium, the cells were subcloned to 96-well plates and then rebulked to 48-well and 24-well plates. The M cell culture is approximately 40–50% positive for cytokeratin expression.

For the ETF bioassay, MIE cells to be assayed were cultured in with D-Valine MEM and 2% FBS in welled flat-bottomed microtiter plates at a rate of 2000 cells/ml or 100 cells/well. IL-2 or ETF were titrated into test wells. Background wells received assay medium only. 0.5 μCi [$^3$H]thymidine/culture was added to the cell cultures 24 hours post cytokine treatment and then harvested after an overnight incubation. Before harvesting, the cells were treated with 1:1 antifoam/NP-40 (antifoam A (1% v/v $H_2O$)/onionic Nonidet P40 (5% v/v H20); Sigma Chemical Co.) to remove them from the plate. The data are expressed as cpm of $^3$H-thymidine incorporated (X $10^{-3}$) in Table 10.

On the basis of the above data, a test was designed to determine if ETF also could protect against radiation (radiotherapy) and chemotherapy induced gut toxicity. From day -3 to day -1, ten 6- to 12-week old female C57B16 mice (Charles River, Boston, Mass.) were injected intraperitonealy with 4 μg ETF twice a day for a total of five injections. Twenty-four hours after the last injection (i.e., on day 0), each of the ten ETF-treated mice and 10 controls received a lethal dose of doxorubicin hydrochloride (30 mk $C_{27}H_{29}NO_{11}$·HCl; SIGMA Chemi cal Co., St. Louis, Mo.). The experimental endpoint was survival to 12 days or death. As shown in FIG. 10, a significantly higher number (80%) of the ETF-pretreated mice survived at least 12 days compared to only 30% of the control mice.

TABLE 9

Vascular permeability of IL-2 and ETF in mice.

|  | lung weights (mg ± SE) | lung cpm (± SE) | blood cpm (± SE) |
|---|---|---|---|
| Control |  |  |  |
| Experiment 1 | 140 ± 3 | 11489 ± 768 | 7013 ± 215 |
| Experiment 2 | 135 ± 2 | 40964 ± 5170 | 20343 ± 763 |
| IL-2 |  |  |  |
| Experiment 1 | 157 ± 3* | 14811 ± 1021* | 7323 ± 380 |
| Experiment 2 | 167 ± 5* | 68150 ± 4455* | 20703 ± 985 |
| ETF |  |  |  |
| Experiment 1 | 141 ± 6† | 11484 ± 909† | 6998 ± 279 |
| Experiment 2 | 130 ± 4† | 38570 ± 3447† | 19547 ± 1029 |

*Significantly different from control group in same experiment.
† Significantly different from IL-2 group in same experiment.

TABLE 10

ETF induction of intestinal epithelial cells.

| cytokine | cpm of $^3$H-thymidine incorporated |
|---|---|
| 200 ng/ml IL-2 | 560.5 |
| 100 ng/ml IL-2 | 456 |
| 50 ng/ml IL-2 | 563.5 |
| none | 358.2 |
| 3 ng/ml ETF | 2255 |
| 1.5 ng/ml ETF | 2484.5 |
| 0.75 ng/ml ETF | 1202.5 |
| none | 358.2 |

EXAMPLE 12

RADIOTHERAPY INDUCED TOXICITY THERAPY

In order to determine whether ETF could protect the gut against radiation induced toxicity, rats were irradiated with 12 Gy to the abdominal cavity on day 0, thereby causing crypt destruction in the intestinal lining. The animals were treated with placebo (rat serum) or ETF twice daily on days -1, 0, 1, 2, and 3. Rats were sacrificed on day 4 and cross sections of the distal small intestinal were made. Crypt microcolonies were counted in the sections along measured distances and data were reported as crypts per mm or crypts per circumference as shown in Table 11. A dose response was seen for ETF with the three highest doses showing more crypts than the rat serum control. The number of crypts with ETF at 800 µg/kg/day was significantly different (p<0.01) from rat serum using Student's t-test. These data indicate that ETF can protect intestinal epithelium from the effects of radiotherapy.

TABLE 11

ETF Protection of Irradiated Intestinal Epithelium in Rats

| Treatment | Animals | Crypts/mm (± SEM) | Crypts/circ (± SEM) |
|---|---|---|---|
| Rat Serum | 7 | 6.20 ± 0.41 | 55.94 ± 7.84 |
| ETF, 200 µg/kg/day | 5 | 4.94 ± 0.64 | 37.82 ± 5.74 |
| ETF, 400 µg/kg/day | 10 | 7.41 ± 1.02 | 63.87 ± 8.26 |
| ETF, 800 µg/kg/day | 10 | *10.76 ± 0.99 | *95.70 ± 9.37 |
| ETF, 1200 µg/kg/day | 5 | 10.36 ± 0.98 | 100.77 ± 15.03 |
| ETF, 1600 µg/kg/day | 5 | 9.97 ± 1.83 | 92.74 ± 18.33 |
| No radiation | 8 | 19.20 ± 0.36 | 163.69 ± 7.39 |

*p < 0.01 compared to rat serum

In a second model of radiation induced gut toxicity, female C57B1/6 mice were treated with a single dose ip of saline or ETF at 50, 100, or 200 µg. After 1 hour mice were exposed to 15 Gy of gamma radiation. Seventy-two hours later, 1% Evans's blue in saline was given iv. at 10 mL/kg. This dye binds to plasma albumin and is confined to the circulation as long as the epithelium is intact. Radiation leads to destruction of the intestinal epithelium thus allowing the dye to pass into the lumen of the gut. Ninety minutes after the dye was given mice were sacrificed and approximately 8 cm of the small intestine was removed. The lumen was ravaged with 1 ml of saline which was collected, sonicated to liberate any dye bound to debris, and clarified by centrifugation. The amount of dye was quantitated by determining the absorbance of the solution at 610 nm, and the data are reported in Table 12. A dose response was seen for ETF. Using ANOVA and Scheffe individual comparisons, 100 and 200 µg doses of ETF were significant compared to control. ETF thus inhibits the radiation induced breakdown of the intestinal epithelium.

TABLE 12

ETF Stimulation of Irradiated Intestinal Epithelium in Mice.

| Treatment | Animals | OD at 610 nm (± SEM) |
|---|---|---|
| Saline | 10 | 0.470 ± 0.083 |
| ETF, 50 µg | 10 | 0.458 ± 0.088 |
| ETF, 100 µg | 9 | 0.148 ± 0.066 |
| ETF, 200 µg | 9 | 0.113 ± 0.039 |
| No radiation | 4 | 0.067 ± 0.014 |

We claim:

1. A method for stimulating T-cells in a patient infected with HIV, comprising administering to a patient infected with HIV an amount of primate epithelium derived T-cell factor polypeptide effective to stimulate T-cell proliferation, wherein said polypeptide is selected from the group consisting of:

(a) a polypeptide comprising the amino acid sequence of SEQ ID NO 3;

(b) a polypeptide comprising the amino acid sequence of SEQ ID NO 6; and (c) a polypeptide encoded by an isolated nucleic acid selected from the group consisting of:

(i) DNA comprising nucleotides 145 through 486 of the DNA sequence of SEQ ID NO 1 or 4;

(ii) DNA that detectably hybridizes to the complement of the DNA of (i) under conditions of high stringency and upon expression encode epithelium-derived T-cell factor; and (iii) DNA that, due to degeneracy of the genetic code, encode a polypeptide encoded by any of the foregoing DNA sequences.

2. The method according to claim 1 wherein said polypeptide comprises the amino acid sequence of SEQ ID No. 3.

3. The method according to claim 1 wherein said polypeptide comprises the amino acid sequence of SEQ ID No. 6.

* * * * *